United States Patent
Wakamiya et al.

(10) Patent No.: US 10,302,666 B2
(45) Date of Patent: *May 28, 2019

(54) SPECIMEN ANALYZER AND SPECIMEN ANALYZING METHOD

(71) Applicant: SYSMEX CORPORATION, Kobe (JP)

(72) Inventors: Yuji Wakamiya, Kobe (JP); Kazutoshi Tokunaga, Kakogawa (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,936

(22) Filed: Feb. 17, 2017

(65) Prior Publication Data

US 2017/0160298 A1    Jun. 8, 2017

Related U.S. Application Data

(63) Continuation of application No. 13/053,921, filed on Mar. 22, 2011, now Pat. No. 9,606,133.

(30) Foreign Application Priority Data

Mar. 25, 2010   (JP) ................................. 2010-070660

(51) Int. Cl.
    *G01N 35/10*    (2006.01)
    *G01N 35/00*    (2006.01)

(52) U.S. Cl.
    CPC . *G01N 35/00613* (2013.01); *G01N 35/00663* (2013.01); *G01N 35/00732* (2013.01); *G01N 35/00871* (2013.01); *G01N 35/1011* (2013.01); *G01N 2035/00673* (2013.01); *G01N 2035/00782* (2013.01); *Y10T 436/117497* (2015.01)

(58) Field of Classification Search
    None
    See application file for complete search history.

(56) References Cited

U.S. PATENT DOCUMENTS

| 2008/0024301 A1 | 1/2008 | Fritchie et al. |
| 2010/0001854 A1 | 1/2010 | Kojima |
| 2012/0133492 A1* | 5/2012 | Onizawa .......... G01N 35/00732 340/10.51 |

FOREIGN PATENT DOCUMENTS

| JP | 7-295866 | * 11/1995 |
| WO | WO-2011013324 | * 2/2011 |

OTHER PUBLICATIONS

Machine-generated English translation of JP-7-295866, Nishitani et al., (1995), pp. 1-4 (Year: 1995).*

* cited by examiner

*Primary Examiner* — Kathryn Wright
(74) *Attorney, Agent, or Firm* — Sughrue Mion, PLLC

(57) ABSTRACT

A sample analyzing method of a sample analyzer for measuring samples, using a reagent container which comprises a writable and readable storage medium, the sample analyzing method including: storing information regarding a remaining amount of a reagent in the reagent container to a memory of the analyzer read from the storage medium; updating the information in the memory in response to an aspiration of the reagent; and writing updated information in the memory to the storage medium when an aspiration of the reagent in a plurality of measurements is completed. The writing of the updated information is postponed until the aspiration of the reagent in the plurality of measurements is completed.

17 Claims, 17 Drawing Sheets

SPECIMEN ANALYZER AND SPECIMEN ANALYZING METHOD

CROSS-REFERENCE TO RELATED APPLICATIONS

This application is a continuation of U.S. application Ser. No. 13/053,921, filed Mar. 22, 2011, which claims priority from Japanese Application No. 2010-070660, filed Mar. 25, 2010. Each of the above-noted applications is incorporated herein by reference in its entirety.

FIELD OF THE INVENTION

The present invention relates to a specimen analyzer and a specimen analyzing method for analyzing a specimen prepared by mixing a sample and a reagent.

BACKGROUND

An analyzer for managing reagents using an RFID tag is conventionally known.

An analyzer described in U.S. patent application publication 2010-0001854 executes a process of acquiring a new reagent remaining amount by subtracting a reagent amount dispensed in a reagent dispensing process for this time from a reagent remaining amount stored in the RFID tag, and rewriting the reagent remaining amount written on the RFID tag to the new reagent remaining amount for every reagent dispensing process.

In such analyzer, a reagent container is positioned at a predetermined position, and the reading of the reagent remaining amount from the RFID tag and the writing of the new reagent remaining amount to the RFID tag are carried out for every reagent dispensing process.

When using the RFID tag for a storage medium, a write error may generally occur, although not frequently. Thus, the risk of occurrence of the write error to the RFID tag may increase if the number of writing to the RFID tag is increased. Therefore, the risk of occurrence of the write error to the RFID tag may increase if the write to the RFID tag is performed for every reagent dispensing process as with the analyzer described above.

SUMMARY OF THE INVENTION

A first aspect of the present invention is a specimen analyzer for continuously measuring a plurality of samples, the specimen analyzer including: a reagent dispenser which dispenses a quantity of reagent to a reaction container which is used for preparing a specimen from a sample and a reagent; a reagent container holder which holds a reagent container which accommodates reagent, the reagent container including a storage medium capable of storing information regarding a remaining amount of the reagent accommodated in the reagent container; a measurement unit which measures the specimen in the reaction container; a memory which stores information regarding a remaining amount of the reagent in the reagent container; a wireless communication unit which wirelessly communicates with the storage medium using radio wave; and a controller; wherein the controller: causes, for conducting continuous measurements, the reagent dispenser to continuously carry out aspiration of the reagent from the reagent container and dispensing of the aspirated reagent to the reaction container, updates the information in the memory in response to an aspiration of the reagent by the reagent dispenser, and causes the wireless communication unit to write the information in the memory to the storage medium when the continuous aspiration is completed.

A second aspect of the present invention is a sample analyzing method, using a reagent container which includes a wirelessly writable and readable storage medium, the sample analyzing method including: reading information from the storage medium to a memory, the information regarding a remaining amount of a reagent in the reagent container; continuously aspirating the reagent from the reagent container; measuring a specimen prepared from the aspirated reagent and a sample; updating the information in the memory in response to an aspiration of the reagent; and writing the information in the memory to the storage medium when the continuous aspiration of the reagent is terminated.

EMBODIMENT OF THE PRESENT INVENTION

The preferred embodiments of the present invention are described hereinafter with reference to the drawings.

In the present embodiment, the present invention is applied to a specimen analyzer for carrying out examinations on various items such as hepatitis B, hepatitis C, tumor marker, and thyroid hormone using samples such as blood.

The specimen analyzer according to the present embodiment bonds magnetic particles (R2 reagent) to a capture antibody (R1 reagent) bonded to an antigen contained in the sample such as blood to be measured, and thereafter, attracts the bound antigen, capture antibody, and the magnetic particles to a magnet (not shown) of a primary BF (Bound Free) separator 11 (see FIG. 1 and FIG. 2) to remove the R1 reagent containing non-reactive (free) capture antibody. The analyzer then bonds the antigen bound with the magnetic particles and the labeled antibody (R3 reagent), and thereafter, attracts the bound magnetic particles, the antigen, and the labeled antibody to a magnet (not shown) of a secondary BF separator 12 to remove the R3 reagent containing non-reactive (free) labeled antibody. The dispersion liquid (R4 reagent) and the light emitting substrate (R5 reagent) that emits light in the reaction process with the labeled antibody are added, and a light emitting amount generated through the reaction of the labeled antibody and the light emitting substrate is measured. The antigen contained in the sample that bonds with the labeled antibody is quantitatively measured through such processes.

A specimen analyzer according to the present embodiment will be hereinafter described with reference to the drawings.

Figure 1:
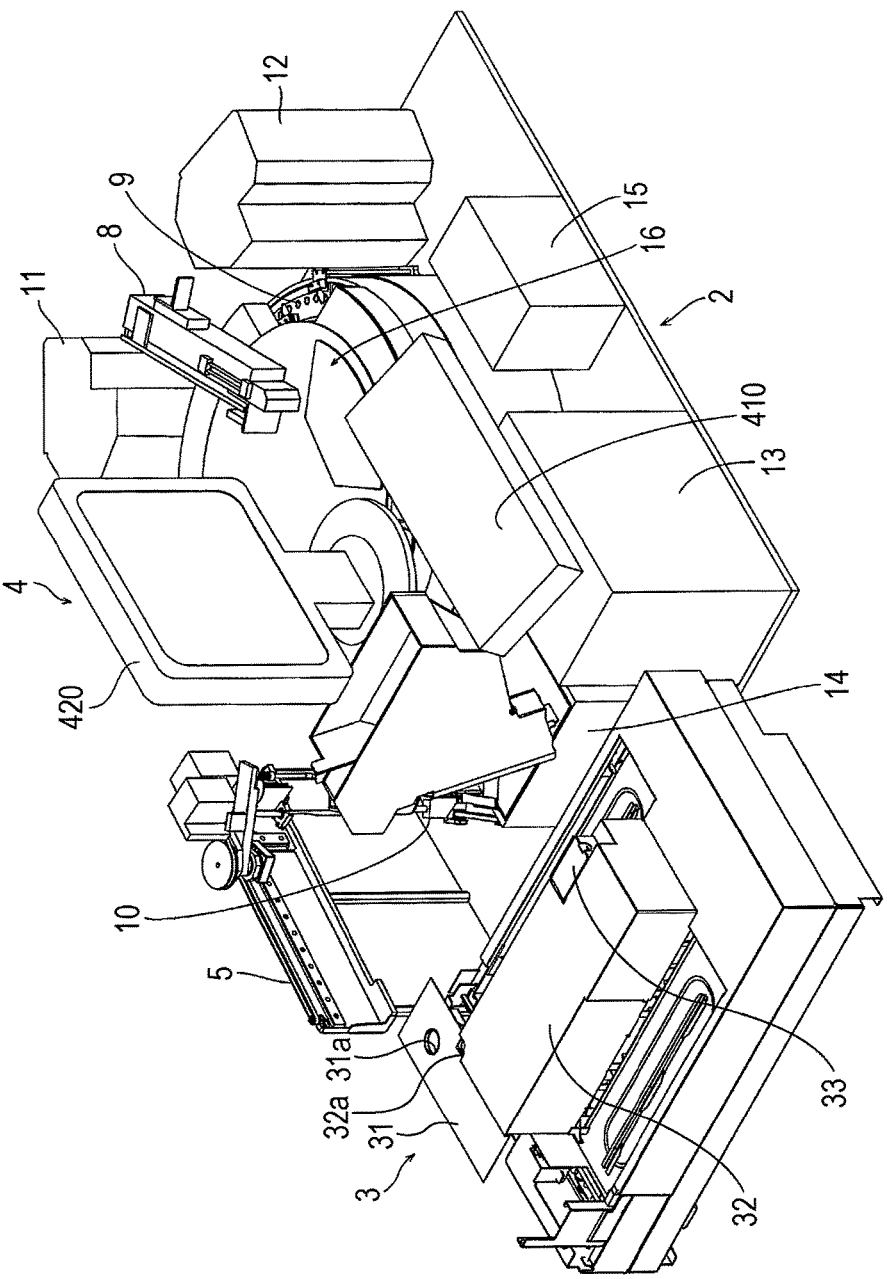
FIG. 1 is a perspective view showing an overall configuration of a specimen analyzer according to an embodiment.

FIG. 1 is a perspective view showing an overall configuration of a specimen analyzer 1.

The specimen analyzer 1 according to the present embodiment includes a measurement mechanism section 2, a sample transport section (sampler) 3 arranged adjacent to the measurement mechanism section 2, and a control device 4 electrically connected to the measurement mechanism section 2.

The sample transport section 3 is configured to be able to transport the rack mounted with a plurality of test tubes containing a sample. The control device 4 is configured by a main body 400 (see FIG. 9), an input unit 410, and a display unit 420.

The control device 4 is connected with a handy type barcode reader 17 (see Fig.9) having the function of reading barcodes.

Figure 2:
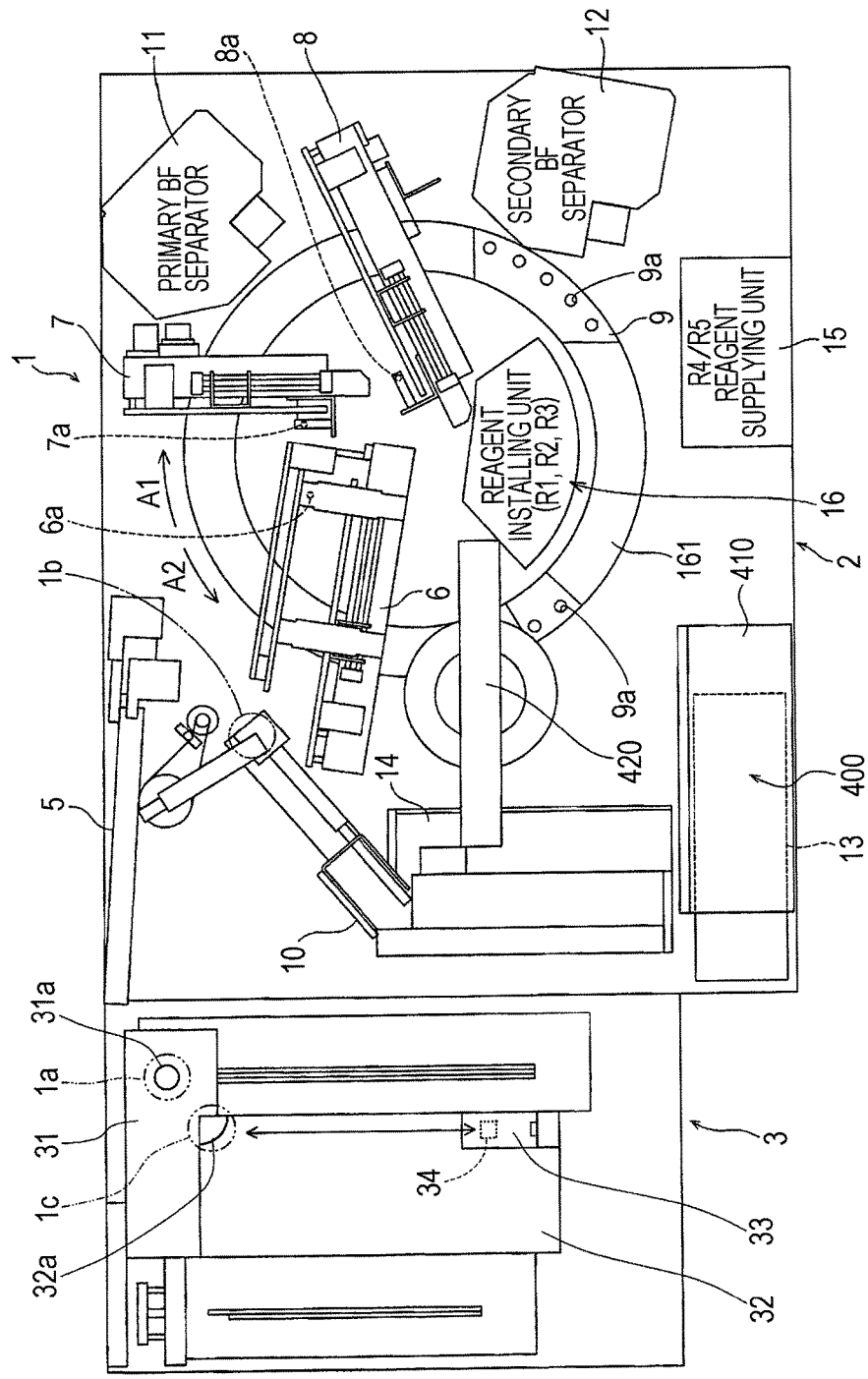
FIG. 2 is a plan view showing a configuration of the measurement mechanism section according to the embodiment seen from the upper side.

FIG. 2 is a plan view showing a configuration of the measurement mechanism section 2 seen from the upper side.

The measurement mechanism section 2 is configured by a sample dispensing arm 5, an R1 reagent dispensing arm 6, an R2 reagent dispensing arm 7, an R3 reagent dispensing arm 8, a reaction unit 9, a cuvette supplying unit 10, a primary BF separator 11, a secondary BF separator 12, a pipette tip supplying unit 13, a detector 14, an R4/R5 reagent supplying unit 15, and a reagent installing unit 16.

The cuvette supplying unit 10 is configured to accommodate a plurality of cuvettes, and sequentially supplies the cuvette to a sample discharging position 1b one by one by means of the sample dispensing arm 5.

The R1 reagent dispensing arm 6 is attached with a pipette 6a for aspirating and discharging the R1 reagent as shown in the figure. The R1 reagent dispensing arm 6 aspirates the R1 reagent installed in the reagent installing unit 16 and dispenses (discharges) the aspirated R1 reagent to the cuvette mounted at the sample discharging position 1b using the pipette 6a.

The pipette tip supplying unit 13 transports the inserted plurality of pipette tips (not shown) to the tip attachment position (not shown) one by one by the sample dispensing arm 5. After a while, the pipette tip is attached to the distal end of the pipette of the sample dispensing arm 5 at the tip attachment position.

The sample dispensing arm 5 attaches the pipette tip at the tip attachment position, aspirates the sample in the test tube transported to a sample aspirating position 1a by the sample transport section 3 through a hole 31a formed at the top plate 31 covering the transport path of the sample transport section 3, and dispenses (discharges) the sample to the cuvette of the sample discharging position 1b dispensed with the R1 reagent by the R1 reagent dispensing arm 6. Such cuvette is transferred to the reaction unit 9 by a catcher (not shown) of the R1 reagent dispensing arm 6.

The R2 reagent dispensing arm 7 is attached with a pipette 7a for aspirating and discharging the R2 reagent as shown in the figure. The R2 reagent dispensing arm 7 uses the pipette 7a to aspirate the R2 reagent installed at the reagent installing unit 16, and to dispense (discharge) the aspirated R2 reagent to the cuvette containing the R1 reagent and the sample.

The reaction unit 9 is formed to a circular ring shape to surround the periphery of the reagent installing unit 16 having a circular shape, as shown in the figure. The reaction unit 9 includes a plurality of cuvette installing portions 9a arranged at a predetermined interval along the outer shape. The cuvette installing portion 9a is circular and is formed to a recess shape so that the cuvette can be inserted thereto, and has a function of warming the cuvette set in the cuvette installing portion 9a to about 42° C. The specimen contained in the cuvette is thus warmed to about 42° C. in the reaction unit 9, and the reaction between the sample and various types of reagents in the cuvette is promoted. The reaction unit 9 is configured to be rotatable in the clockwise direction (direction of arrow A1), so that the cuvette set in the cuvette installing portion 9a can be moved to the respective processing position where various processes (dispensing of reagent, etc.) are carried out.

When the cuvette containing the sample, the R1 reagent, and the R2 reagent is transferred from the reaction unit 9 to the primary BF separator 11 by the catcher (not shown), the primary BF separator 11 separates (B/F separates) the non-reacting R1 reagent (unnecessary component) and the magnetic particles from the specimen in the cuvette.

The R3 reagent dispensing arm 8 is attached with a pipette 8a for aspirating and discharging the R3 reagent as shown in the figure. The R3 reagent dispensing arm 8 aspirates the R3 reagent installed in the reagent installing unit 16 using the pipette 8a. The R3 reagent dispensing arm 8 uses the pipette 8a to dispense (discharge) the aspirated R3 reagent to the cuvette transferred from the primary BF separator 11 to the reaction unit 9.

When the cuvette containing the specimen after the B/F separation by the primary BF separator 11 and the R3 reagent is transferred to the secondary BF separator 12 from the reaction unit 9 by the catcher (not shown), the secondary BF separator 12 separates (B/F separates) the non-reacting R3 reagent (unnecessary component) and the magnetic particles from the specimen in the cuvette.

The R4/R5 reagent supplying unit 15 dispenses the R4 reagent and the R5 reagent in order to the cuvette containing the specimen after the B/F separation by the secondary BF separator 12 with a tube (not shown).

The detector 14 measures the amount of antigen contained in a sample by obtaining the light generated in the reaction process of the labeled antibody bound to the antigen of the sample performed with a predetermined process and the light emitting substrate with a photo multiplier tube.

A circular cover 161 is arranged on the upper surface of the reagent installing unit 16 so as to cover both the reagent installing unit 16 and the reaction unit 9. An opening for the R1 to R3 reagent dispensing arms to aspirate the reagent and an opening for the R1 to R3 reagent dispensing arms to move the cuvette or perform the dispensing process are formed at predetermined areas of the cover 161.

In the present embodiment, a measurement (hereinafter referred to as "interrupting measurement") of interrupting the normal continuous measurement to preferentially measure the sample is prepared in addition to the continuous measurement (hereinafter, "continuous measurement) of a plurality of samples performed when the sample is aspirated from the test tube transported to the sample aspirating position 1a. In other words, the continuous measurement is temporarily stopped to measure the sample to be preferentially measured (hereinafter referred to as "priority sample") even if the sample to perform the continuous measurement (hereinafter referred to as "normal sample") exists in the sample transport section 3.

A lid 33 is installed on the right end of the near side of the top plate 32 arranged near the center of the sample transport section 3. When performing the interrupting measurement, the user opens the lid 33 and sets the test tube containing the priority sample in the holder 34 positioned immediately under the lid 33. When the lid 33 is closed, the test tube held at the holder 34 is transported towards the far side. The priority sample in the test tube transported to the priority sample aspirating position 1c by the holder 34 is aspirated by the sample dispensing arm 5 through a cutout 32a formed at the right end of the far side of the top plate 32. Thereafter, the priority sample is measured through procedures similar to the above. After the aspiration of the test tube containing the priority sample is completed, the test tube is transported to immediately under the lid 33 from the priority sample aspirating position 1c by the holder 34. Thereafter, the user opens the lid 33 and takes out the test tube held at the holder 34.

Figure 3:
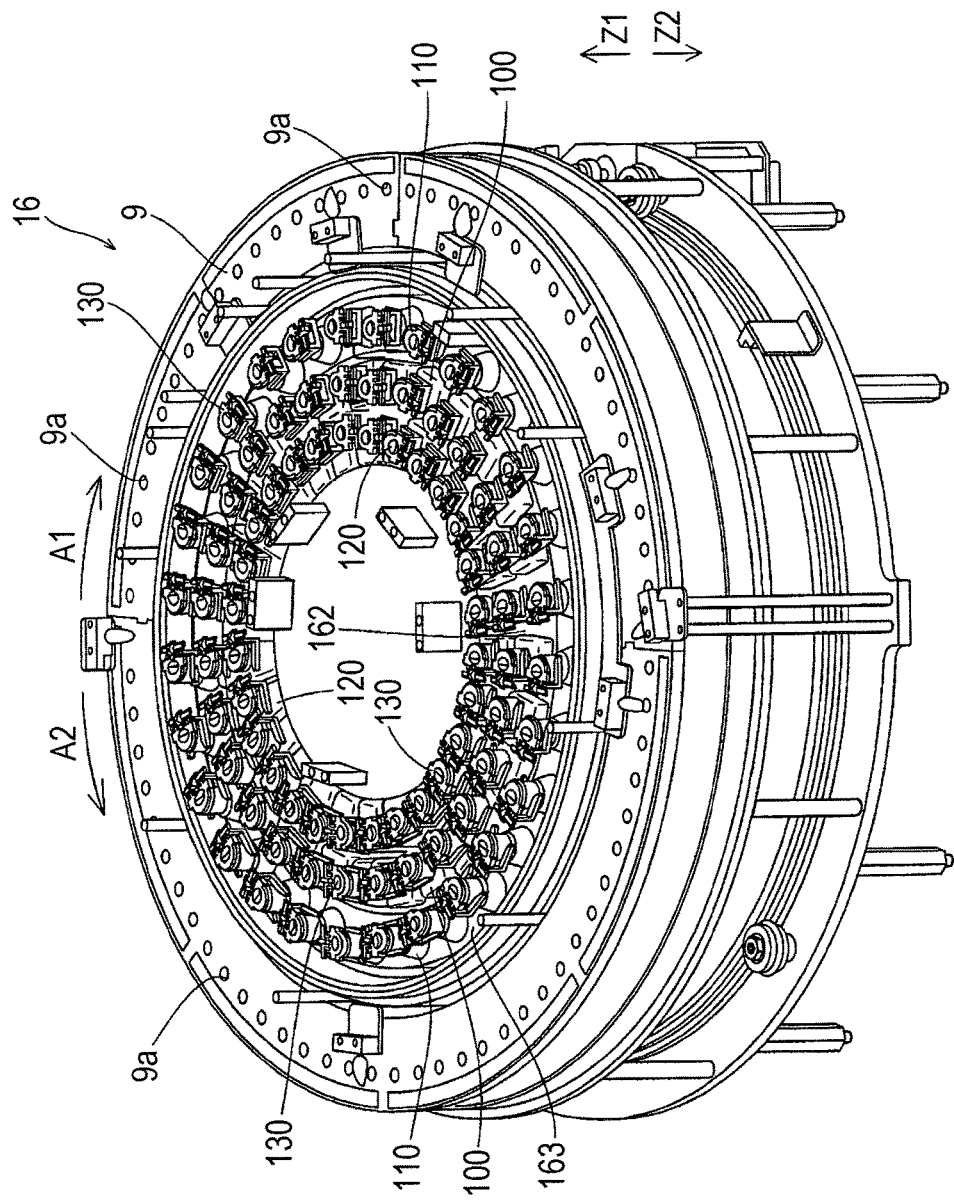
FIG. 3 is a perspective view of when the cover is removed from the reagent installing unit according to the embodiment.

FIG. 3 is a perspective view of when the cover 161 is removed from the reagent installing unit 16. The reagent installing unit 16 includes an inner side table 162 and an outer side table 163 of a circular ring shape when seen from the upper side.

The inner side table 162 is formed with a plurality of holders capable of holding the R1 reagent container 100 containing the R1 reagent, and a plurality of holders capable of holding the R3 reagent container 120 containing the R3 reagent. According to such holder, the plurality of R1 reagent containers 100 on the inner side table 162 is held in a circular ring shape so as to surround the outer side of the R3 reagent container 120 arrayed in a circumferential shape, as shown in the figure. The plurality of R1 reagent containers 100 of the inner side table 162 are held in a state adjacent to the R3 reagent container 120 in the radial direction, to be hereinafter described.

The inner side table 162 is configured to be horizontally rotatable in the clockwise direction (direction of arrow A1) and the counterclockwise direction (direction of arrow A2). Specifically, the inner side table 162 is configured to be rotatable by a first stepping motor 162a (see FIG. 8). When the inner side table 162 is rotated (turned), the R1 reagent container 100 and R3 reagent container 120 are rotated (turned) at the same angle in the same direction with each other.

The outer side table 163 is formed with a plurality of holders capable of holding the R2 reagent container 110 accommodating the R2 reagent. According to such holder, the R2 reagent containers 110 on the outer side table 163 is held in a circular ring shape so as to surround the outer side of the R1 reagent container 100 arrayed in a circumferential shape, as shown in the figure.

The outer side table 163 is configured to be horizontally rotatable in the clockwise direction (direction of arrow A1) and the counterclockwise direction (direction of arrow A2). Specifically, the outer side table 163 is configured to be rotatable by a second stepping motor 163a (see FIG. 8). The outer side table 163 is rotatable independent from the inner side table 162. The outer side table 163 has a function of rotating (turning) while stirring the R2 reagent contained in the R2 reagent container 110 it holds.

Antennas 162b, 163b (see FIG. 8) for reading and writing the unique information and the reagent management information stored in the RFID tag, to be described later, are installed on the inner side of the inner side table 162 and the outer side of the outer side table 163. The arrangement of the antennas 162b, 163b will be hereinafter described with reference to FIG. 6.

Figure 4:
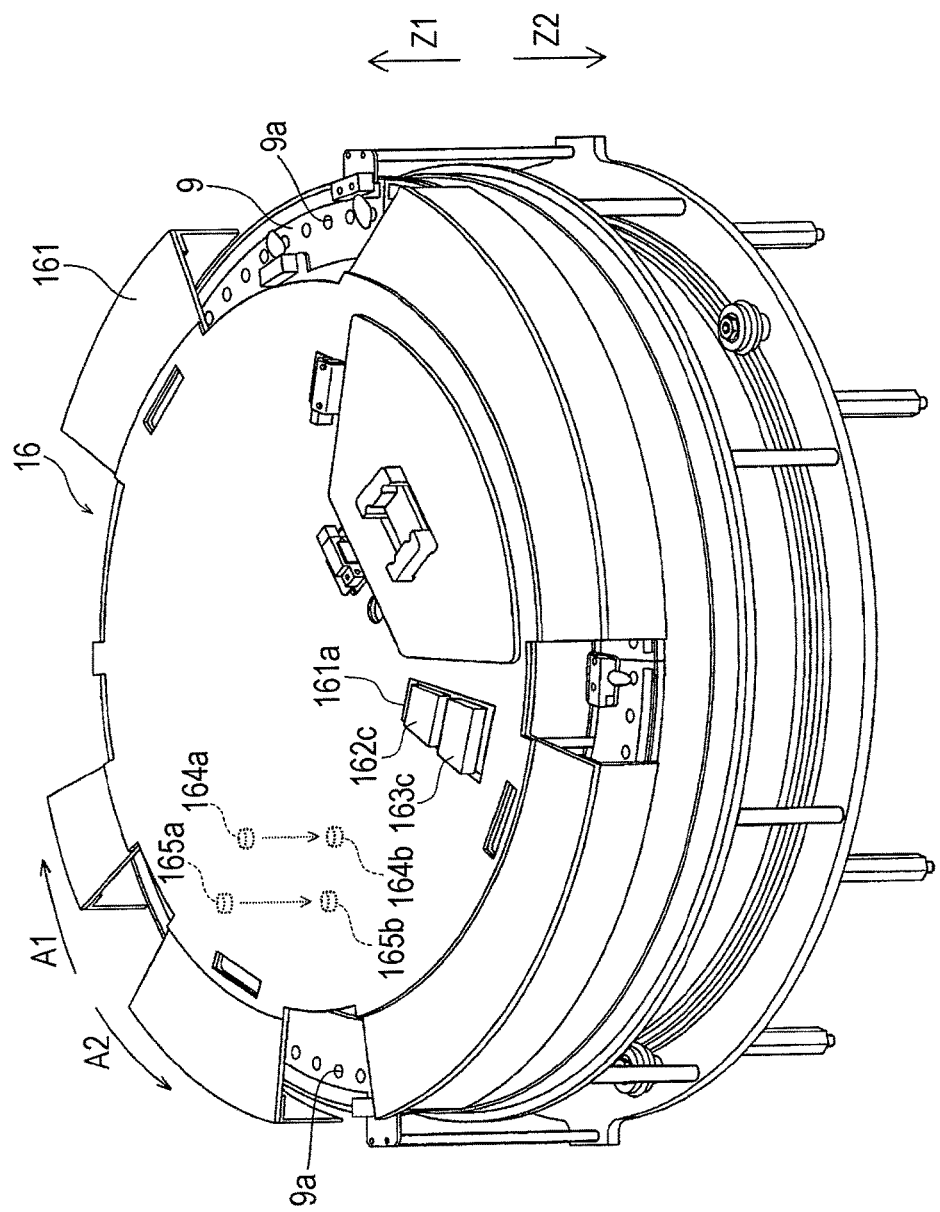
FIG. 4 is a perspective view of when the cover is attached to the reagent installing unit according to the embodiment.

FIG. 4 is a perspective view of when the cover 161 is attached to the reagent installing unit 16.

As shown in the figure, the cover 161 is formed with an input/output hole 161a so that the R1 to R3 reagent containers can be installed to the inner side table 162 or the outer side table 163 from the outside. Mounting boards 162c, 163c that can move in the perpendicular direction are installed in the region immediately below the input/output hole 161a. The mounting boards 162c, 163c are configured to be movable between the height of the cover 161 and the height of the inner side table 162 and the outer side table 163.

When the input/output hole 161a and the mounting boards 162b, 163b are configured in such manner, the user can install or take out the R1 to R3 reagent containers from the outer side on the upper side of the cover 161. In other words, the R1 reagent container 100 and the R3 reagent container 120 (R2 reagent container 110) are mounted on the mounting board 162b (163b) positioned at the height of the cover 161, as shown in the figure, and the mounting board 162b (163b) is moved to the lower side, so that the reagent containers are set in the inner side table 162 (outer side table 163). The R1 reagent container 100 and the R3 reagent container 120 (R2 reagent container 110) set in the inner side table 162 (outer side table 163) are moved to the outer side on the upper surface of the cover 161 when the mounting board 162b (163b) is moved to the upper side. The R1 to R3 reagent containers then can be installed or taken out.

As shown in the figure, the light emitting portions 164a, 165a of the transmissive sensor are installed on the back surface side of the cover 161, and the light receiving portions 164b, 165b of the transmissive sensor are installed at the reagent installing unit 16 on the lower side of the inner side table 162 and the outer side table 163. The light exit from the light emitting portions 164a, 165a is received by the light receiving portions 164b, 165b. Each holder of the inner side table 162 and the outer side table 163 is formed with an opening (not shown) that passes in the up and down direction. When the holder for holding the fitted R1 reagent container 100 and the R3 reagent container 120, to be described later, is positioned between the light emitting portion 164a and the light receiving portion 164b, it can be recognized that the fitted R1 reagent container 100 and the R3 reagent container 120 are set at the holder. When the holder for holding the R2 reagent container 110 is positioned between the light emitting portion 165a and the light receiving portion 165b, it can be recognized that the R2 reagent container 110 is set in the holder.

Figure 5A:
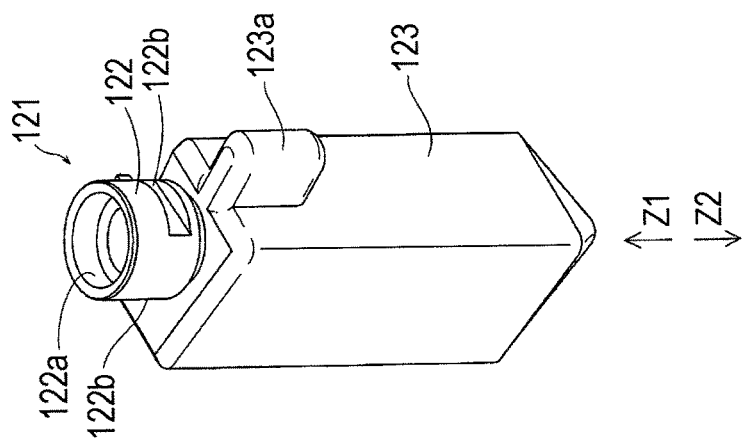
FIGS. 5A, 5B and 5C are perspective views respectively showing the configuration of the R1 reagent container, the R2 reagent container, and the R3 reagent container according to the various embodiments.
Figure 5B:
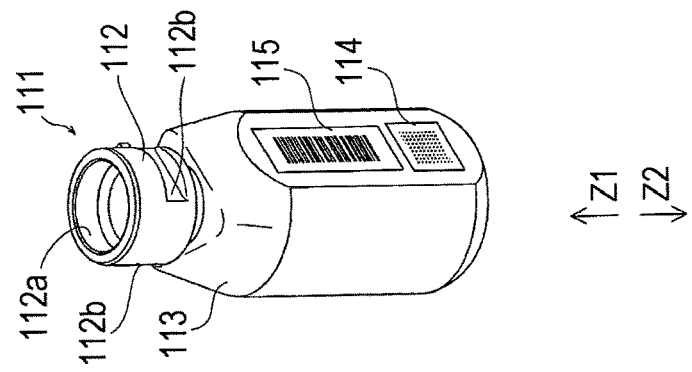
Figure 5C:
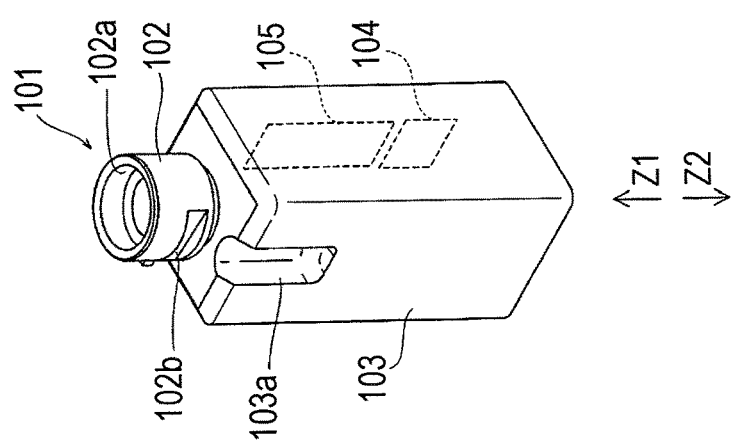

FIGS. 5A, 5B, and 5C are perspective views respectively showing the configuration of the R1 reagent container 100, the R2 reagent container 110, and the R3 reagent container 120. In the figures, the illustration of the lid member is omitted from each reagent container for the sake of convenience.

With reference to FIG. 5A, the container main body 101 of the R1 reagent container 100 includes a cylindrical portion 102 formed to a substantially cylindrical shape on the upper side, and an accommodating portion 103 for accommodating the reagent on the lower side. The upper end of the cylindrical portion 102 includes a circular opening 102a, and a pair of cutout grooves 102b extending in the horizontal direction is formed symmetrically at the side surface of the cylindrical portion 102. The lid member (not shown) is attached to the cylindrical portion 102 of the container main body 101 by way of a supporting member (not shown) to be engaged to the cutout groove 102b.

A cutout 103a extending downward (direction of arrow Z2) from the upper surface of the accommodating portion 103 is formed at one side surface of the accommodating portion 103 on the side formed with the cutout grooves 102b, as shown in the figure. The cutout 103a is configured to receive the projection 123a of the R3 reagent container 120, to be described later. The R1 reagent container 100 and the R3 reagent container 120 can be easily arrayed so as to be adjacent to each other with a predetermined spacing by fitting the projection 123a of the R3 reagent container 120 in the cutout 103a of the R1 reagent container 100.

The RFID (Radio Frequency IDentification) tag 104 and the barcode label 105 are attached on the side surface opposite to the side surface formed with the cutout 103a, as shown in the figure. The RFID tag 104 is written with unique information and reagent management information, where the unique information and the reagent management information of the RFID tag 104 are read and written through the radio wave by the antenna 162b, to be described later. The reagent management information is also written to the barcode label 105. The reagent management information of the barcode label 105 is read by the barcode reader 17. The unique information and the reagent management information will be described later with reference to FIG. 7.

With reference to FIG. 5B, the container main body 111 of the R2 reagent container 110 is configured substantially similar to the R1 reagent container 100. In other words, the RFID tag 114 and the barcode label 115 having the configuration similar to the R1 reagent container 100 are attached to the accommodating portion 113. The RFID tag 114 is written with unique information and reagent management information, where the unique information and the reagent management information of the RFID tag 114 are read and written through the radio wave by the antenna 163b. The reagent management information is also written to the barcode label 115. The reagent management information of the barcode label 115 is read by the barcode reader 17. A cutout corresponding to the cutout 103a of the R1 reagent container 100 is not formed in the accommodating portion 113. The cylindrical portion 112 includes an opening 112a and a pair of cutout grooves 112b.

With reference to FIG. 5C, the container main body 121 of the R3 reagent container 120 is configured substantially similar to the R1 reagent container 100. The cylindrical portion 122 includes an opening 122a and a pair of cutout grooves 122b. A projection 123a extending downward (direction of arrow Z2) from the upper surface of the accommodating portion 123 is formed at one side surface of the accommodating portion 123 on the side formed with the cutout grooves 122b, as shown in the figure. The projection 123a is configured to fit into the cutout 103a of the R1 reagent container 100.

The R1 reagent container 100 and the R3 reagent container 120 are set in the holder of the inner side table 162 while always being fitted by the cutout 103a and the projection 123a from the start of use by the user. The R1 reagent container 100 and the R3 reagent container 120 are always used in the same measurement. Since only the R3 reagent container 120 does not need to be individually identified from such usage state, the RFID tag and the barcode level are not attached to the R3 reagent container 120. In this case, the fitted R1 reagent container 100 and the R3 reagent container 130 (hereinafter referred to as "R1/R3 reagent container") is identified by the reagent management information read from the RFID tag and the barcode label attached to the R1 reagent container 100.

Figure 6:
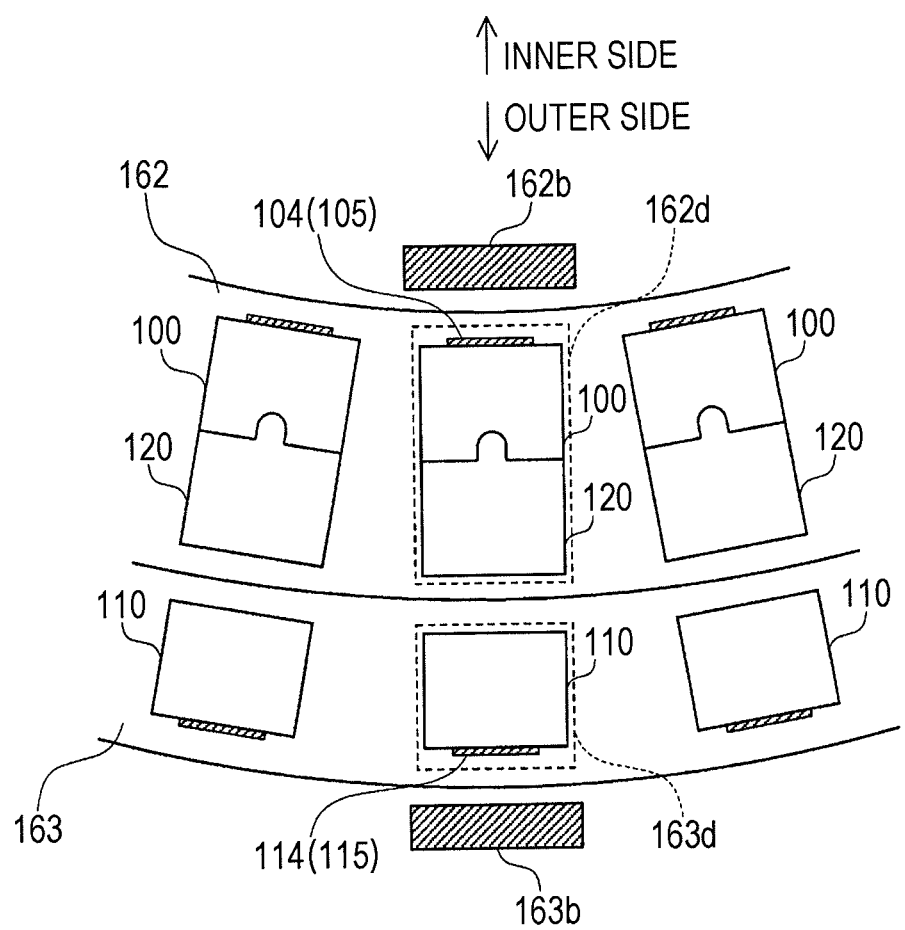
FIG. 6 is a plan view schematically showing the configuration of when the vicinity of the antennas according to the embodiment is seen from the upper side.

FIG. 6 is a plan view schematically showing the configuration of when the vicinity of the antennas 162b, 163b is seen from the upper side.

As shown in the figure, the antennas 162b, 163b are on the inner side of the inner side table 162 and the outer side of the outer side table 163, respectively, and are installed at the reagent installing unit 16. The antenna 162b reads and writes the reagent management information by wireless communication through the radio wave with respect to the RFID tag 104 of the R1/R3 reagent container positioned at the opposing position (read and write position 162d) on the inner side table 162. As described above, the RFID tag of the R1/R3 reagent container is attached to the R1 reagent container 100. The antenna 163b reads and writes the reagent management information by wireless communication through the radio wave with respect to the RFID tag 104 of the R1 reagent container 100 positioned at the opposing position (read and write position 163d) on the outer side table 163.

If the reagent management information of the RFID tags 104, 114 cannot be read, the barcode labels 105, 115 are used. In other words, if the RFID tags 104, 114 are not read by the antennas 162b, 163b due to damage or the like, the user takes out the reagent container from the reagent installing unit 16 and causes the barcode information to be read by the handy type barcode reader 17 connected to the control unit 4. Thus, the reagent container can be identified even if the RFID tag cannot be read.

The read and write position 162d is set at a position different from the position where the reagent is aspirated by the R1 reagent dispensing arm 6 and the R3 reagent dispensing arm 8. The read and write position 163d is set at a position different from the position where the reagent is aspirated by the R2 reagent dispensing arm 7.

Figure 7:
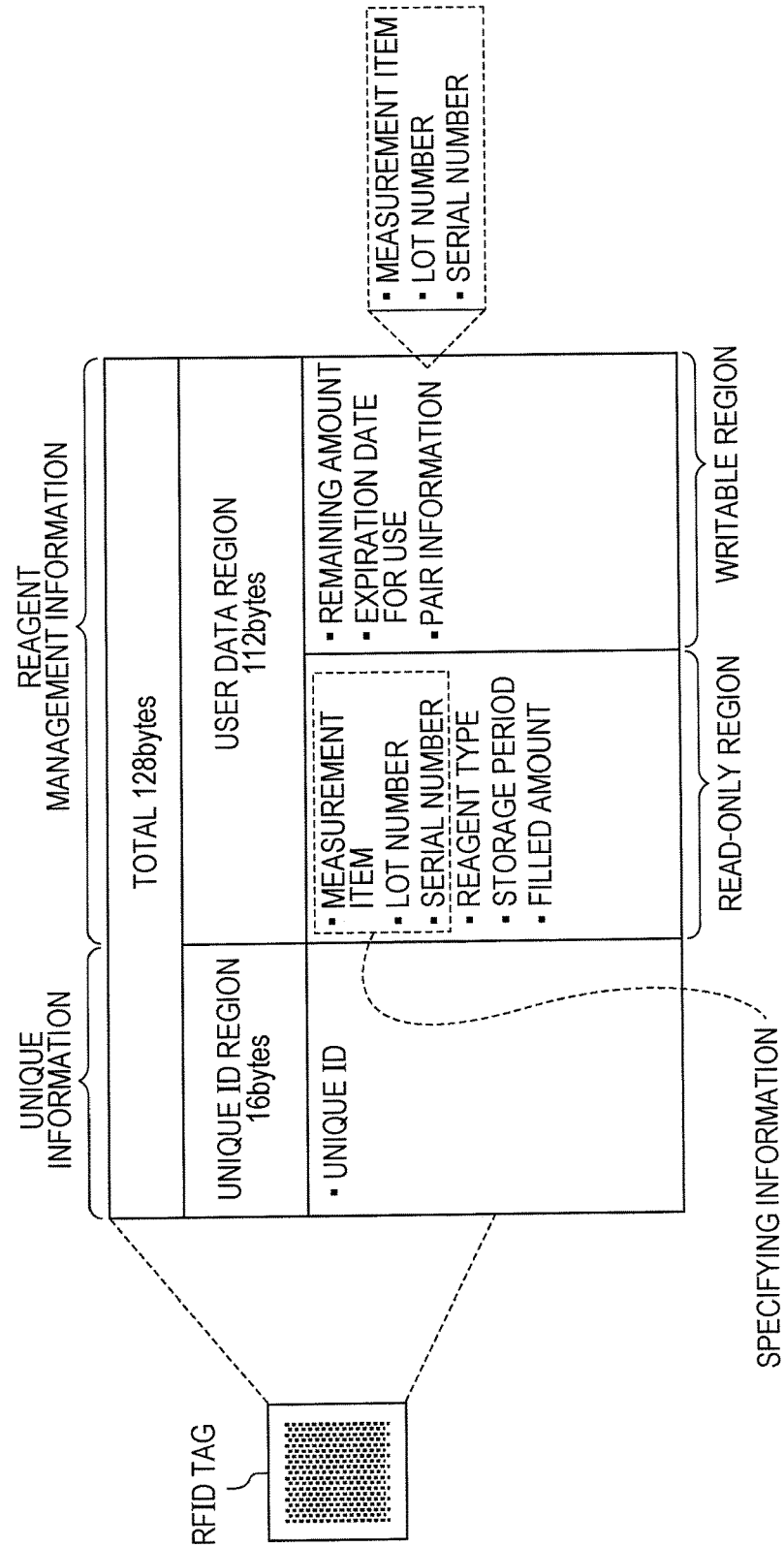
FIG. 7 is a conceptual view showing the unique information and the reagent management information stored in the RFID tag according to the present embodiment.

FIG. 7 is a conceptual view showing the unique information and the reagent management information stored in the RFID tags 104, 114.

As shown in the figure, the RFID tags 104, 114 are configured to store 128 bytes of information. Among the storage capacity of 128 bytes, 16 bytes are assigned for the unique ID region indicating the unique information, and 112 bytes are assigned for the user data region indicating the reagent management information. The unique ID region is the region where the unique ID for individually identifying the RFID tag is stored, and only read can be carried out. The user data region is the region where the user can freely write information. The user data region is set with a region (read only region) where only read is carried out and write is not carried out, and a region (writeable region) where both read and write are carried out.

The measurement item, the lot number, the serial number, the reagent type, the storage period, and the filled amount are recorded in the read only region. The remaining amount, the expiration date for use and the pair information are written in the writable region. The information is not written in the writable region of the RFID tag attached to the reagent container installed for the first time in the inner side table 162 and the outer side table 163. The information same as in the read-only region stored in the RFID tags 104, 114 is stored in the barcode labels 105, 115.

The measurement item shows the measurement item performed with the reagent accommodated in the reagent container attached with the RFID tag. The R1/R3 reagent container and the R2 reagent container 110 are uniquely identified by the measurement item, the lot number, and the serial number (hereinafter referred to as "specifying information"). The serial number is the number that can uniquely identify the reagent container within the range of the same measurement item and the same lot number, where the R1/R3 reagent container and the R2 reagent container 110 having the same measurement item and the same lot number are packaged and provided to the user. The R1/R3 reagent container and the R2 reagent container 110 having the same measurement item and the same lot number are used as a pair in terms of the nature of usage.

The reagent type shows whether the reagent container attached with the RFID tag is the R1/R3 reagent container or the R2 reagent container 110. The storage period shows the period the reagent can be stored. The filled amount shows the number of measurements that can be carried out with the reagent. The remaining amount shows the remaining number of measurements that can be carried out with the reagent. The expiration date for use shows the date until the reagent can be used. The expiration date for use is set when the relevant reagent starts to be used.

The R1 reagent container 100 and the R3 reagent container 120 are used in the fitted state and are used for the same measurement, as described above, and thus the storage period, the filled amount, the remaining amount, and the expiration date for use of the R1 reagent container 100 and the R3 reagent container 120 are the same. Thus, only the storage period, the filled amount, the remaining amount, and the expiration date for use of the R1 reagent container are stored in the RFID tag 104.

The specifying information of the reagent container that forms a pair with the relevant reagent container is written to the item of the pair information. In other words, the specifying information of the RFID tag 114 of the R2 reagent container 110 used as a pair is written to the pair information of the RFID tag 104 of the R1/R3 reagent container installed in the inner side table 162 for the first time. In other words, the specifying information of the RFID tag 104 of the R1/R3 reagent container used as a pair is written to the pair information of the RFID tag 114 of the R2 reagent container installed in the outer side table 163 for the first time.

Figure 8:
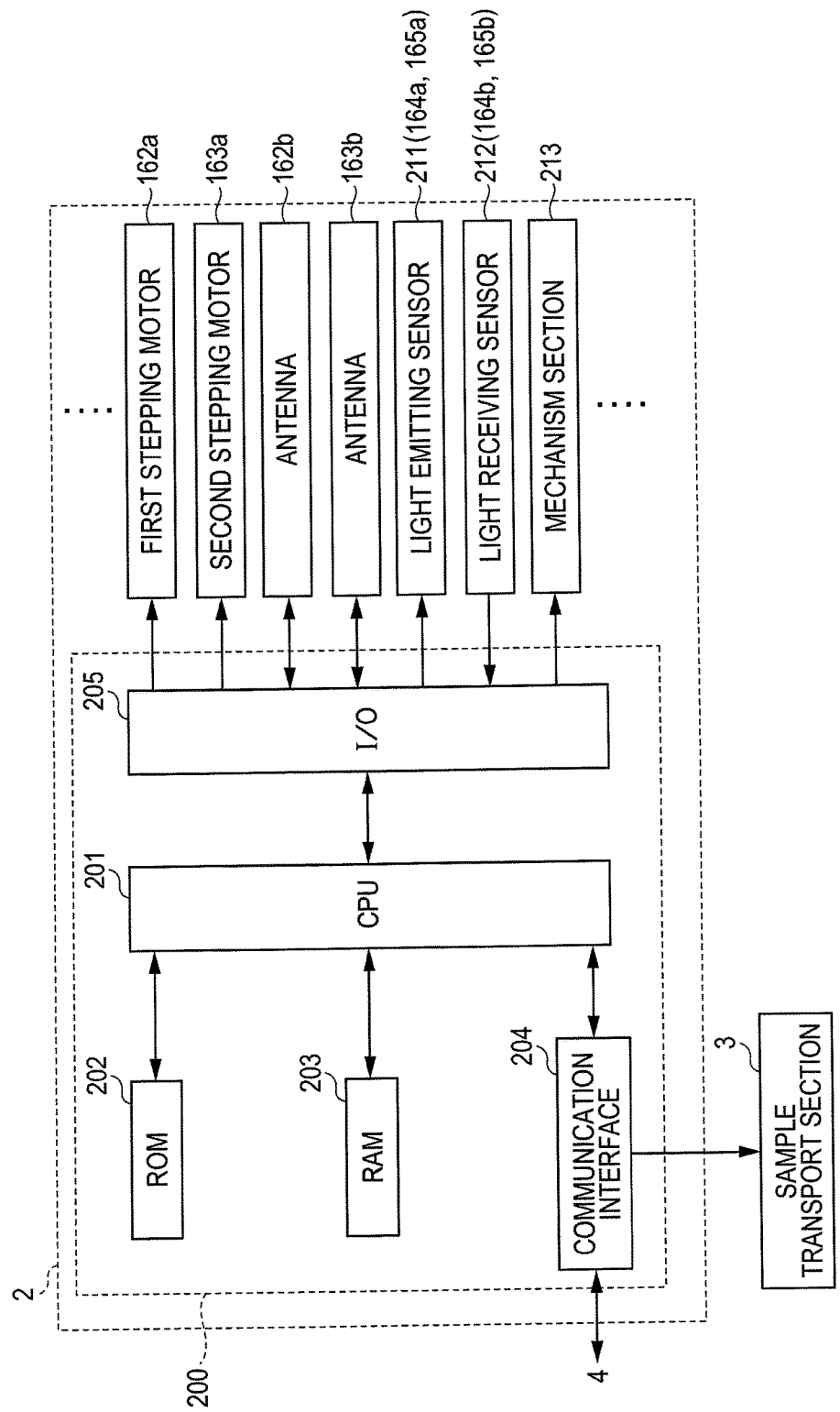
FIG. 8 is a view showing a circuit configuration of the measurement mechanism section according to the embodiment.

FIG. 8 is a view showing a circuit configuration of the measurement mechanism section 2.

The measurement mechanism section 2 includes a control unit 200, a first stepping motor 162a, a second stepping motor 163a, antennas 162b, 163b, a light emitting sensor 211, a light receiving sensor 212, and a mechanism section 213. The control unit 200 includes a CPU 201, a ROM 202, a RAM 203, a communication interface 204, and an I/O interface 205.

The CPU 201 executes computer programs stored in the ROM 202 and the computer programs loaded in the RAM 203. The RAM 203 is used to read out the computer programs recorded on the ROM 202, and is also used as a work region of the CPU 201 when executing the computer programs. The RAM 203 is a built with a database (hereinafter referred to as "reagent DB") regarding the unique information and the reagent management information of the held reagent container in correspondence with each holder of the inner side table 162 and the outer side table 163.

The communication interface 204 is connected to the sample transport section 3 and the control device 4. The CPU 201 transmits optical information (data of light emission amount generated by reaction of the labeled antibody and light emitting substrate) of the sample to the control device 4, and receives signals from the control device 4 through the communication interface 204. The CPU 201 also transmits a signal for instructing drive to the sample transport section 3 through the communication interface 204.

The CPU 201 is connected to the first stepping motor 162a, the second stepping motor 163a, the antennas 162b, 163b, the light emitting sensor 211, the light receiving sensor 212, and the mechanism section 213 through the I/O interface 205.

The first stepping motor 162a and the second stepping motor 163a are independently driven by the control of the CPU 201. The antennas 162b, 163b read the reagent management information of the RFID tags 104, 114 by the control of the CPU 201. The reagent management information read by the antennas 162b, 163b are output to the CPU 201 through the I/O interface 205, and stored in the RAM 203. The light emitting sensor 211 includes light emitting portions 164a, 165a, and emits light by the control of the CPU 201. The light receiving sensor 212 includes light receiving portions 164b, 165b, and the detection signal of the light receiving sensor 211 is output to the CPU 201 through the I/O interface 205. The mechanism section 213 includes other mechanisms of the measurement mechanism section 2, and is driven by the control of the CPU 201.

Figure 9:
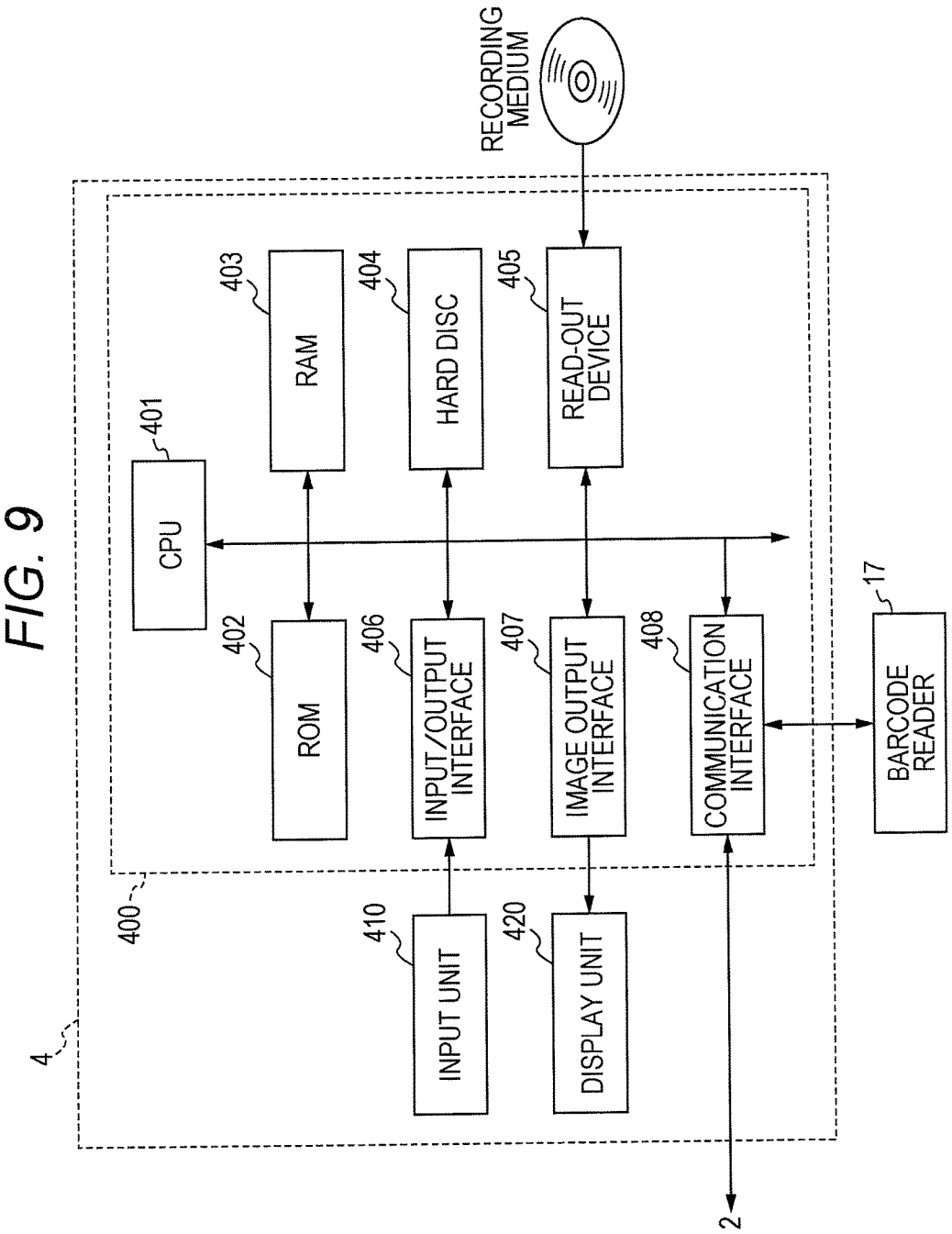
FIG. 9 is a view showing a circuit configuration of a control device according to the embodiment.

FIG. 9 is a view showing a circuit configuration of the control device 4.

The control device 4 includes a personal computer, and is configured by a main body 400, an input unit 410, and a display unit 420. The main body 400 includes a CPU 401, a ROM 402, a RAM 403, a hard disc 404, a read-out device 405, an input/output interface 406, an image output interface 407, and a communication interface 408.

The CPU 401 executes computer programs stored in the ROM 402 and the computer programs loaded in the RAM 403. The RAM 403 is used to read out the computer programs recorded on the ROM 402 and the hard disc 404. The RAM 403 is also used as a work region of the CPU 401 when executing the computer programs.

The hard disc 404 is installed with various computer programs to be executed by the CPU 401 such as operating system and application program, as well as data used in executing the computer program. In other words, the program for performing display and the like on the display unit 420 based on the reagent DB transmitted from the measurement mechanism section 2, the program for transmitting instruction to the measurement mechanism section 2 based on the instruction received from the user through the input unit 410, and the like are installed.

The read-out device 405 is configured by CD drive, DVD drive, and the like, and is able to read out computer programs and data recorded on a recording medium. The input unit 410 including keyboard and mouse is connected to the input/output interface 406, so that the operator can use the input unit 410 to input data to the control device 4. The image output interface 407 is connected to the display unit 420 configured by a display and the like, and outputs a video signal corresponding to the image data to the display unit 420. The display unit 420 displays the image based on the input video signal. The communication interface 408 enables transmission and reception of data with respect to the measurement mechanism section 2 and the barcode reader 17.

Figure 10:
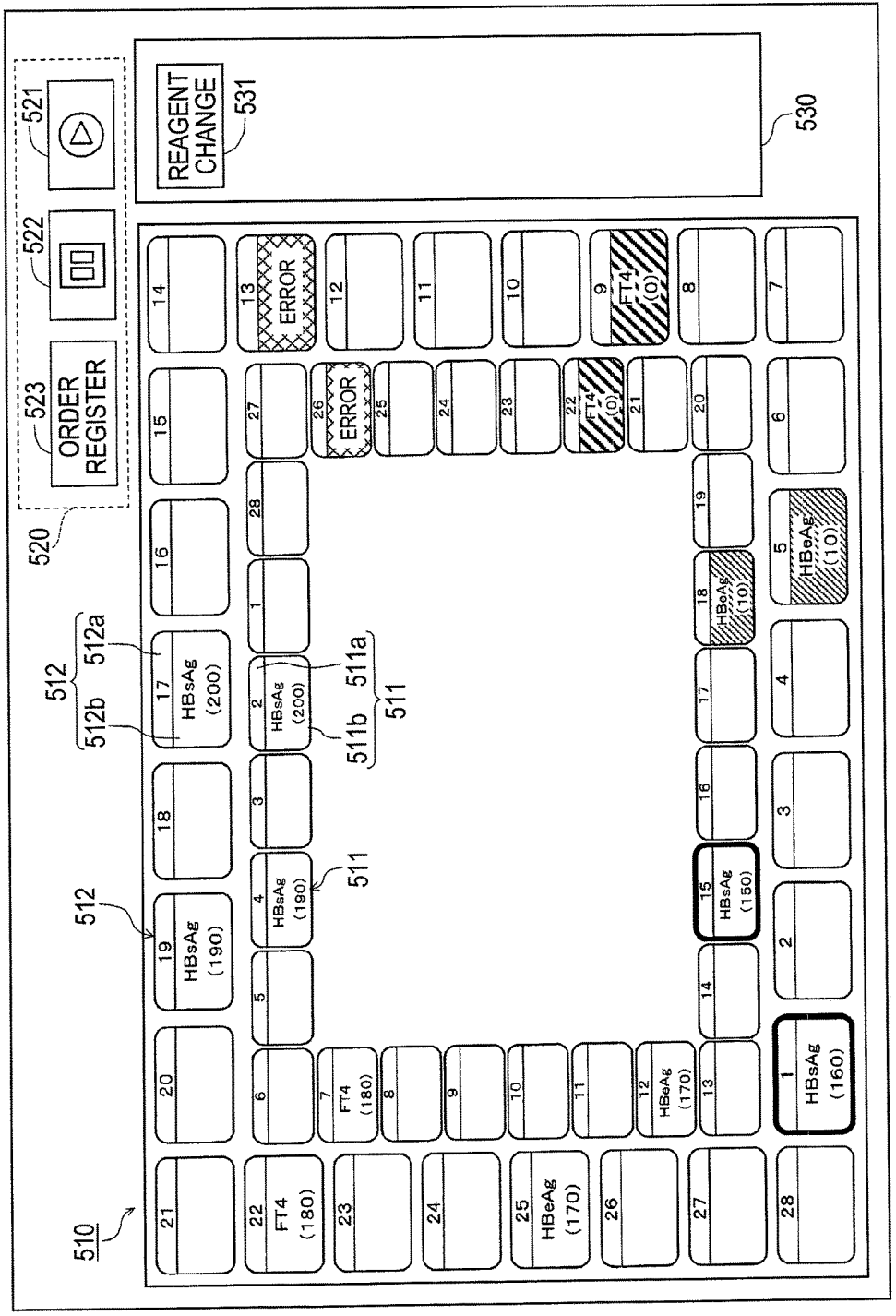
FIG. 10 is an illustrative view of a screen showing the arrangement state of the reagent displayed on the display unit of the control device according to the embodiment.

FIG. 10 is an illustrative view of a screen showing the arrangement state of the reagent displayed on the display unit 420 of the control device 4. The screen showing the arrangement state of the reagent includes a reagent arrangement display region 510, an operation instruction region 520, and a reagent change instruction region 530.

28 R1/R3 reagent marks 511 are displayed in a circular ring form on the inner side (hereinafter referred to as "inner side region") of the reagent arrangement display region 510, and 28 R2 reagent marks 512 are displayed in a circular ring form on the outer side (hereinafter referred to as "outer side region") of the reagent arrangement display region 510. The R1/R3 reagent mark 511 and the R2 reagent mark 512 respectively correspond to the R1/R3 reagent container held in each holder of the inner side table 162 and the R2 reagent container 120 held in each holder of the outer side table 163.

The R1/R3 reagent mark 511 includes a position display portion 511a for displaying the position of the holder, and a content display portion 511b for displaying the measurement item and the remaining amount of the RFID tag 104 of the R1 reagent container 100 held at the holder. Similarly, the R2 reagent mark 512 includes a position display portion 512a for displaying the position of the holder, and a content display portion 512b for displaying the measurement item and the remaining amount of the RFID tag 114 of the R2 reagent container 110 held at the holder.

When determined as useable without any problem in the measurement based on the reading result of the RFID tags 104, 114, the Rl/R3 reagent mark 511 and the R2 reagent mark 512 corresponding to the holder of the reagent container are displayed as shown at the holding position (2) of the inner side region and the holding position (17) of the outer side region. When determined that the reagent container to be used as a pair does not exist as a result of the reading result of the RFID tags 104, 114, the R1/R3 reagent mark 511 and the R2 reagent mark 512 corresponding to the holder of the relevant reagent container are surrounded with a thick line as shown at the holding position (15) of the inner side region and the holding position (1) of the outer side region.

When determined that the reagent container is not set based on the light emitting sensor 211 and the light receiving sensor 212, the content display portion corresponding to the relevant holder is blank. When determined that the remaining amount of reagent container is few based on the reading result of the RFID tags 104, 114, the content display portion corresponding to the relevant holder is displayed with shaded lines of narrow interval, as shown at the holding position (18) of the inner side region and the holding position (5) of the outer side region. When determined that the remaining amount in the reagent container is zero or the date for use is expired, the content display portion corresponding to the relevant holder is displayed with shaded lines of wide interval as shown at the holding position (22) of the inner side region and the holding position (9) of the outer side region. If the RFID tags 104, 114 cannot be used due to reading error, the content display portion corresponding to the relevant holder is displayed with a lattice and "error" is displayed in the content display portion as shown at the holding position (26) of the inner side region and the holding position (13) of the outer side region.

The operation instruction region 520 includes a measurement start button 521, a measurement pause button 522, and an order register button 523.

When the measurement start button 521 is pushed, the continuous measurement instruction is transmitted from the control device 4 to the measurement mechanism section 2, the continuous measurement is started at the control device 4.

The continuous measurement in the present embodiment means measuring a plurality of samples based on the measurement order registered in the control device 4 by means of the specimen analyzer 1. The measurement order is at least set with which measurement item to measure for each of the plurality of samples. The measurement order is registered in the control device 4 at the order registration screen, to be described later, or the measurement order stored in a host computer is registered in the control device 4 by being received through the network and the like.

When the measurement pause button 522 is pushed, the measurement pause instruction is transmitted from the control device 4 to the measurement mechanism section 2, and the measurement being performed in the measurement mechanism section 2 is stopped. If the measurement start button 521 is pushed while the measurement is stopped, the measurement pause cancel instruction is transmitted from the control device 4 to the measurement mechanism section 2, and the measurement that was stopped is resumed.

When the order register button 523 is pushed, the order registration screen (not shown) is displayed. The order register screen includes a screen where the sample to perform the continuous measurement and the sample to perform the interrupting measurement can be registered. When performing the interrupting measurement, the user first registers the sample (priority sample) to perform the interrupting measurement on the order register screen. Thereafter, the user opens the lid 33 shown in FIG. 2, set the test tube containing the priority sample in the holder 34, and closes the lid 33. The priority sample is then measured. In this case, when the test tube containing the priority sample is set in the holder 34 and the lid 33 is closed by the user, the interrupting measurement instruction is transmitted from the control device 4 to the measurement mechanism section 2, and the interrupting measurement is carried out in the control device 4.

The reagent change instruction region 530 includes a reagent change button 531.

When the reagent change button 531 is pushed, the reagent change instruction is transmitted from the control device 4 to the measurement mechanism section 2, and the changing of the reagent is started. In other words, the R1 to R3 reagent containers to be newly set in the measurement mechanism section 2 are mounted on the mounting boards 162c, 163c, and then held in the open holder of the inner side table 162 and the outer side table 163 by the mounting boards 162c, 163c. The R1 to R3 reagent containers specified to be taken out are positioned on the cover 161 by the mounting boards 162c, 163c. At least one open space is provided in the holder of the inner side table 162 and the outer side table 163 so that a new reagent container can always be set.

Figure 11:
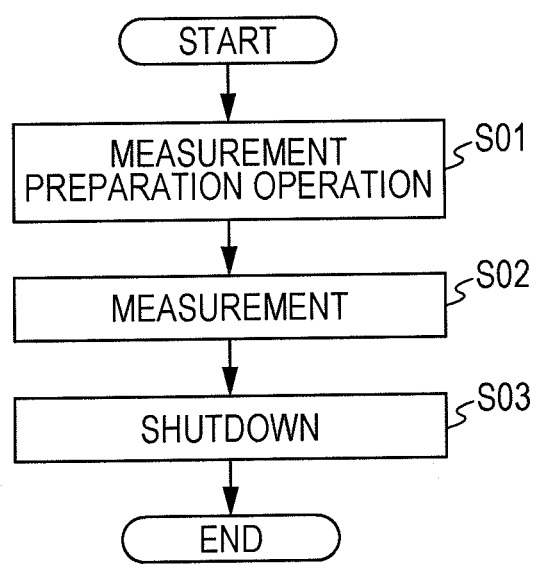
FIG. 11 is a flowchart showing the operation of the specimen analyzer according to the embodiment.

FIG. 11 is a flowchart showing the operation of the specimen analyzer 1. When the power of the specimen analyzer 1 is turned ON by the user, the specimen analyzer 1 performs a measurement preparation operation (S01). Specifically, the CPU 201 reads out the RFID tag 104 of the R1/R3 reagent container and the RFID tag 114 of the R2 reagent container 110, and stores the reagent management information corresponded to each holder in the RAM 203 as a reagent DB. The CPU 201 identifies the R1/R3 reagent container and the R2 reagent container 110 as a pair based on the read reagent management information, and stores the pair information in the reagent DB.

The remaining amounts of the R1 reagent container 100 and the R3 reagent container 120 are separately stored in the reagent DB. In other words, the remaining amount of the reagent management information of the R1/R3 reagent container read in SO1 is stored in the reagent DB as the remaining amount of the R1 reagent container 100 and the remaining amount of the R3 reagent container 120.

The specimen analyzer 1 is then in the standby state so as to be able to execute the measurement of the sample. When the instruction to measure the sample is made from the user, the specimen analyzer 1 executes the measurement operation of the sample (S02). The sample is measured in the measurement mechanism section 2. The details on the measurement operation of the sample by the measurement mechanism section 2 will be hereinafter described.

The user makes an instruction of the shutdown process to the specimen analyzer 1 when all the measurements of the sample to be measured are finished. The specimen analyzer 1 executes the shutdown process (S03) and the operation of the specimen analyzer 1 is terminated.

Figure 12:
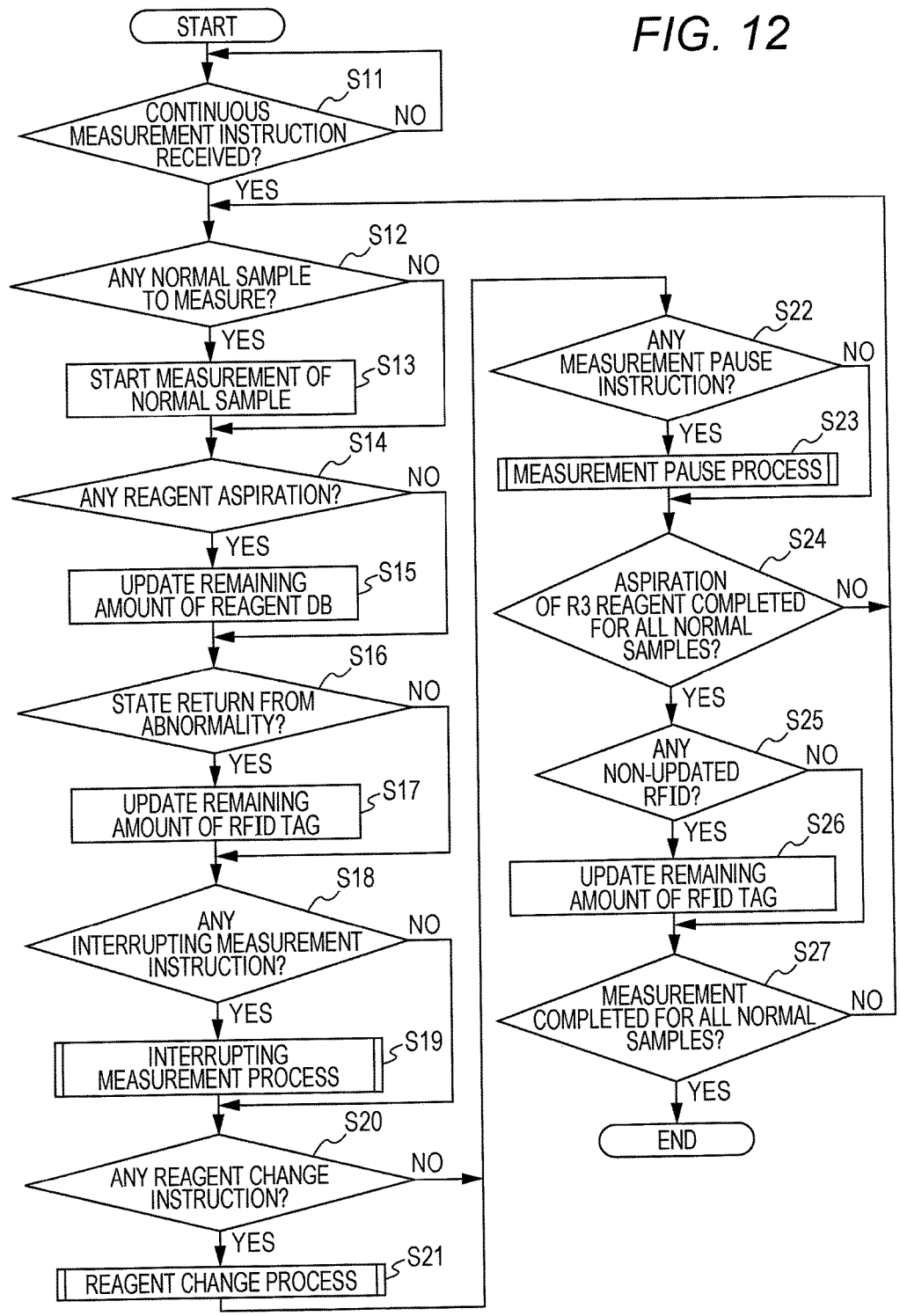
FIG. 12 is a flowchart showing the measurement operation by the measurement mechanism section according to the embodiment.

FIG. 12 is a flowchart showing the measurement operation by the measurement mechanism section 2.

The CPU 201 waits the process until receiving the continuous measurement instruction from the control device 4 (S11). When receiving the instruction to start the continuous measurement (S11: YES), the CPU 201 determines whether or not the normal sample to measure exists (S12). If the normal sample to measure exists (if test tube is positioned at the sample aspirating position 1a, S12: YES), the measurement of the normal sample is started. In other words, the normal sample in the test tube positioned at the sample aspirating position la is aspirated, the sample and the R1 to R3 reagents are mixed, and the measurement is carried out by the detector 14.

The CPU 201 then determines whether or not the reagent is aspirated from the R1 to R3 reagent container (S14). If one of the reagents is aspirated (S14: YES), the CPU 201 updates (reduces) the remaining amount of R1 to R3 in the reagent DB stored in the RAM 203 according to the aspirating amount for the reagent container in which aspiration was carried out (S15). In this case, the remaining amount in the reagent DB is updated every time the reagent is aspirated. The sample is measured in parallel for every plurality of normal samples in the aspirating order at the sample aspirating position 1a.

During the continuous measurement, the CPU 201 determines whether or not the measurement mechanism section 2 state returned from abnormal (S16). The CPU 201 determines whether or not the state return button 632 (FIG. 15) to be described later is pushed. If the determination is YES, the CPU 201 writes the remaining amount of each reagent container in the reagent DB of the RAM 203 of immediately before the abnormality occurs in the RFID tags 104, 114 through the antennas 162b, 163b (S17). In other words, the CPU 201 compares the reagent DB of immediately before the abnormality occurs and the reagent DB newly built in S01, and corresponds the reagent container in the reagent DB of immediately before the abnormality occurs and the reagent container in the reagent DB newly built. The remaining amount of the corresponding reagent container in the reagent container DB of immediately before the abnormality occurs is sequentially written to the RFID tag of each reagent container held in each holder of the reagent installing unit 16 (inner side table 162 and outer side table 163). In this case, the remaining amount of the R1 reagent container 100 in the reagent DB of immediately before the abnormality occurs is written to the RFID tag 104. Furthermore, the CPU 201 writes the remaining amount of the corresponding reagent container of the reagent DB of immediately before the abnormality occurs in the remaining amount in the reagent container of the new reagent DB. The remaining amount in the reagent in the RFID tag and the reagent DB is updated in such manner.

When receiving the interrupting measurement instruction from the control device 4 during the continuous measurement (S18: YES), the CPU 201 performs the "interrupting measurement process" (S19). When the reagent change button 531 is pushed and the reagent change instruction is received from the control device 4 during the continuous measurement (S20: YES), the CPU 201 performs the "reagent change process" (S21). The CPU 201 determines as YES in S20 and performs the "reagent change process" even if the reagent is aspirated and the remaining amount in the reagent DB becomes zero. When receiving the measurement pause instruction from the control device 4 during the continuous measurement (S22: YES), the CPU 201 performs the "measurement pause process" (S23). The "interrupting measurement process", the "reagent change process", and the "measurement pause process" will be described later with reference to FIGS. 13A, 13B, and 14A. The CPU 201 waits the process until the dispensing of the R3 reagent is completed in all measurements (S24). If the dispensing of the R3 reagent is completed in all measurements, the remaining amount of each reagent container in the reagent DB is fixed since the R1 to R3 reagent will not be aspirated in the continuous measurement.

If the dispensing of the R3 reagent is completed in all measurements (S24: YES), the CPU 201 determines whether or not there is an RFID tag in which the remaining amount of reagent is not updated (S25), and writes the remaining amount in the reagent DB stored in the RAM 203 to the corresponding RFID tags 104, 114 through the antennas 162b, 163b (S26) if there is a non-updated RFID tag (S25: YES).

The CPU 201 then determines whether all the measurements are completed (S27), and proceeds the process to step S12 if all the measurements are not completed (S27: NO), and terminates the measurement operation by the measurement mechanism section 2 if all the measurements are completed (S27: YES). The measurement operation by the measurement mechanism section 2 is repeatedly carried out during the operation of the measurement mechanism section 2.

Figure 13A:
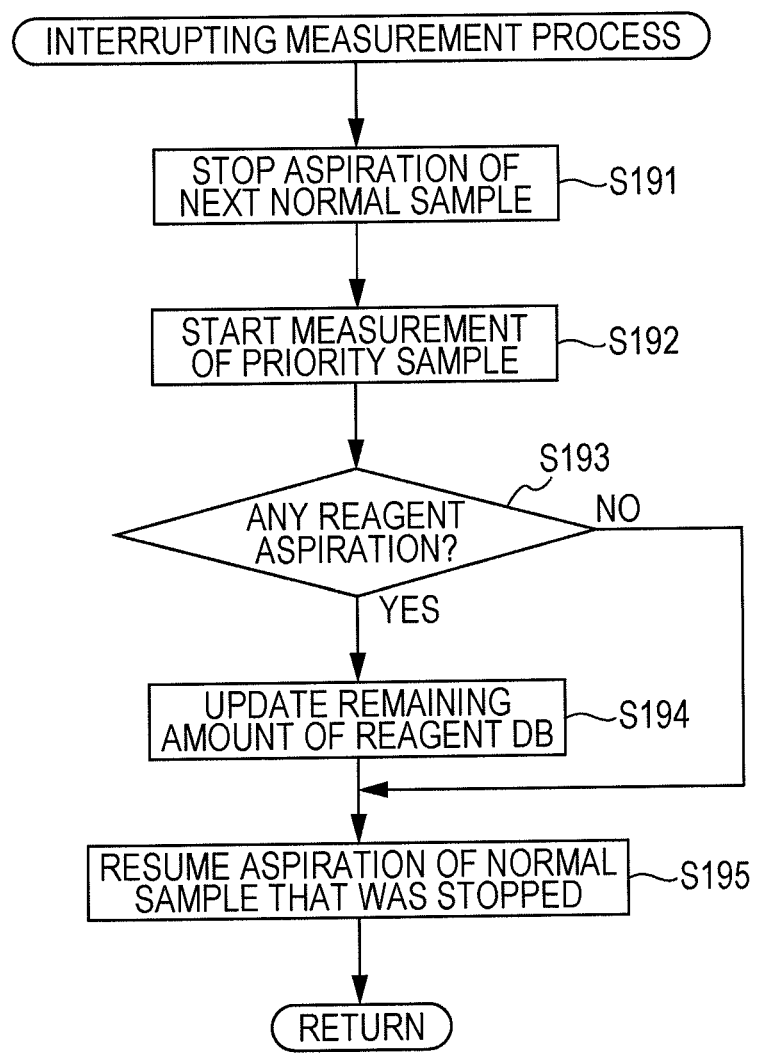
FIG. 13A is a flowchart showing an interrupting measurement process according to the embodiment.

FIG. 13A is a flowchart showing the "interrupting measurement process".

The CPU 201 first stops the aspiration of the next normal sample at the sample aspirating position 1a (S191). If the sample is not aspirated by the sample dispensing arm 5 at the time point the interrupting measurement is instructed, the sample dispensing arm 5 waits without aspirating the next sample. If the sample is being aspirated by the sample dispensing arm 5 at the time point the interrupting measurement is instructed, the sample dispensing arm 5 dispenses the relevant sample in the cuvette and waits without aspirating the next sample. However, the measurement process of the normal sample already dispensed into the cuvette is continued.

The CPU 201 then starts the measurement of the priority sample (S192). In other words, the priority sample in the test tube positioned at the priority sample aspirating position is aspirated, the priority sample and the R1 to R3 reagents are mixed, and the measurement is carried out by the detector 14. The CPU 201 then determines whether or not the reagent is aspirated from the R1 to R3 reagent containers (S193). If the reagents are aspirated from the R1 to R3 reagent containers (S193: YES), the CPU 201 updates (reduces) the remaining amount of R1 to R3 in the reagent DB stored in the RAM 203 according to the aspirating amount for the reagent container in which aspiration was carried out (S194). The measurement of the priority sample started in S192 is carried out parallel to the continuous measurement already being carried out.

The CPU 201 then resumes the aspiration of the normal sample that was stopped (S195). In other words, when the priority sample is aspirated, the aspiration of the normal sample that was stopped is resumed.

Figure 13B:
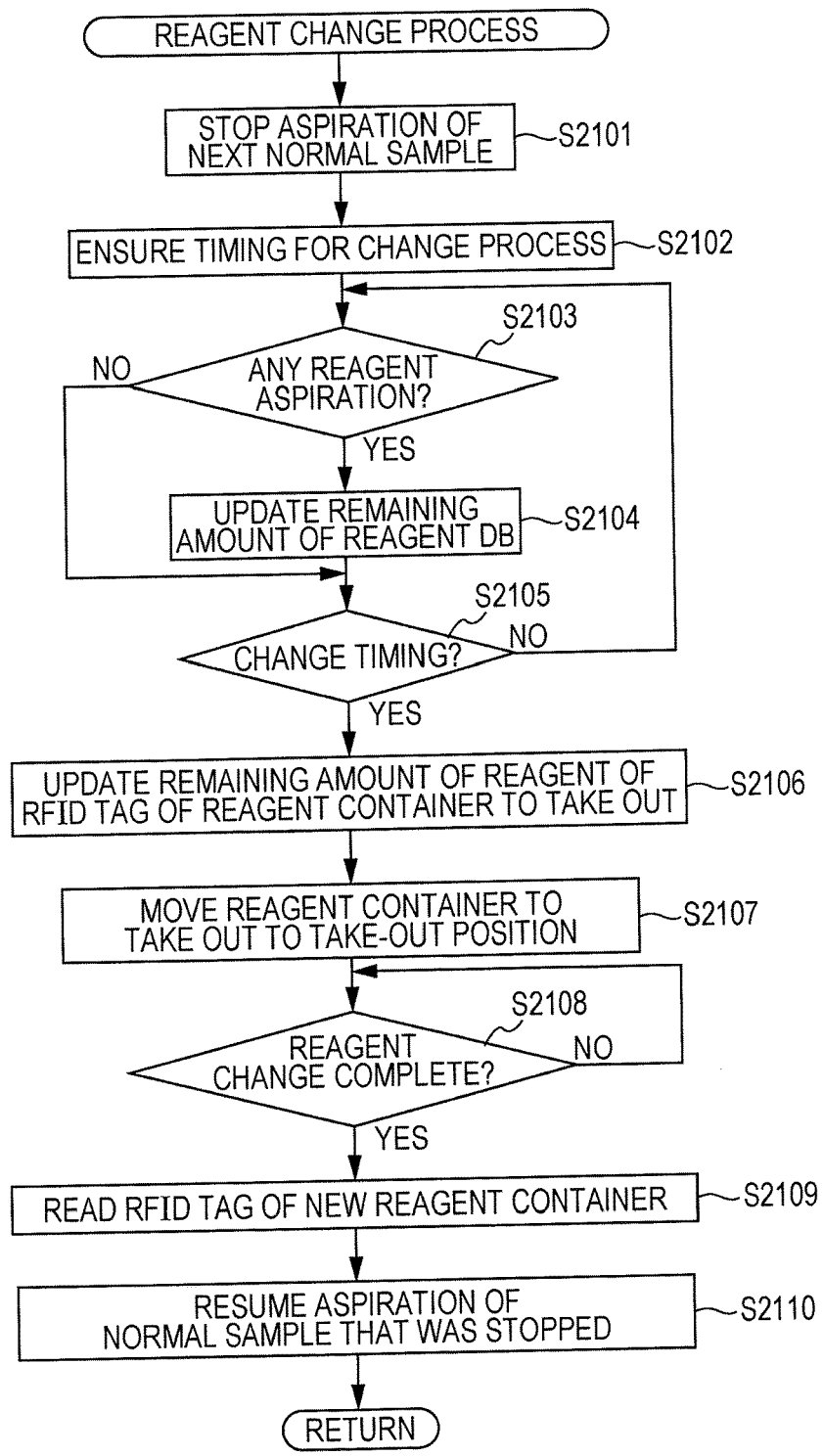
FIG. 13B is a flowchart showing a reagent change process according to the embodiment.

FIG. 13B is a flowchart showing the "reagent change process".

The CPU 201 first stops the aspiration of the next normal sample (S2101). In this case, the CPU 201 moves the mounting board 162c or 163c upward so that a new reagent container can be mounted on the mounting board 162c or 163c. In parallel therewith, the CPU 401 of the control device 4 displays a pop-up screen (not shown) that can instruct the start of reagent change on the display unit 420. The user mounts a new reagent container in the mounting board 162c or 163c, specifies the reagent container to take out through the pop-up screen, and instructs the start of reagent change. When the start of reagent change is instructed, the CPU 201 moves the mounting board 162c or 163c downward, so that the new reagent container is held in the holder of the inner side table 162 or the outer side table 163.

The CPU 201 then ensures the timing to change the reagent (S2102). The CPU 201 ensures a predetermined time (time necessary for measurement of one sample or two samples, 18 seconds per sample) from when the dispensing of the R3 reagent is completed as the time necessary for the reagent change process for the sample currently being measured in the measurement mechanism section 2.

The CPU 201 then determines whether or not the reagent is aspirated from the R1 to R3 reagent containers (S2103). When the reagent is aspirated from the R1 to R3 reagent containers (S2103: YES), the CPU 201 updates (reduces) the remaining amount of R1 to R3 in the reagent DB stored in the RAM 203 according to the aspirating amount for the reagent container in which aspiration was carried out (S2104).

The CPU 201 determines whether it is the timing to change the reagent, that is, whether the dispensing of the R3 reagent is completed for the sample currently being measured in the measurement mechanism section 2 (S2105). The CPU 201 proceeds the process to step 52103 if the dispensing of the R3 reagent is not completed (S2105: NO), and updates the remaining amount of the RFID tag of the reagent container to take out (S2106) if the dispensing of the R3 reagent is completed (S2105: YES). In other words, the CPU 201 writes the remaining amount in the reagent DB in the RFID tags 104, 114 of the reagent container to take out through the antennas 162b, 163b. A while after, the CPU 201 moves the relevant reagent container to a region immediately below the input/output hole 161a (S2107). The moved reagent container is positioned on the cover 161 by the mounting board 162c or 163c.

The CPU 201 then waits the process until the reagent change is completed (S2108). In other words, the process is waited until the reagent container is positioned on the cover 161 by the mounting bard 162c or 163c. When the reagent change is completed (S2108: YES), the CPU 201 reads the RFID tag of the newly held reagent container through the antennas 162c, 163c (S2109). The reagent management information on the newly held reagent container is thereby stored in the reagent DB. A while after, the CPU 201 resumes the aspiration of the normal sample while that was stopped (S2110).

Figure 14A:
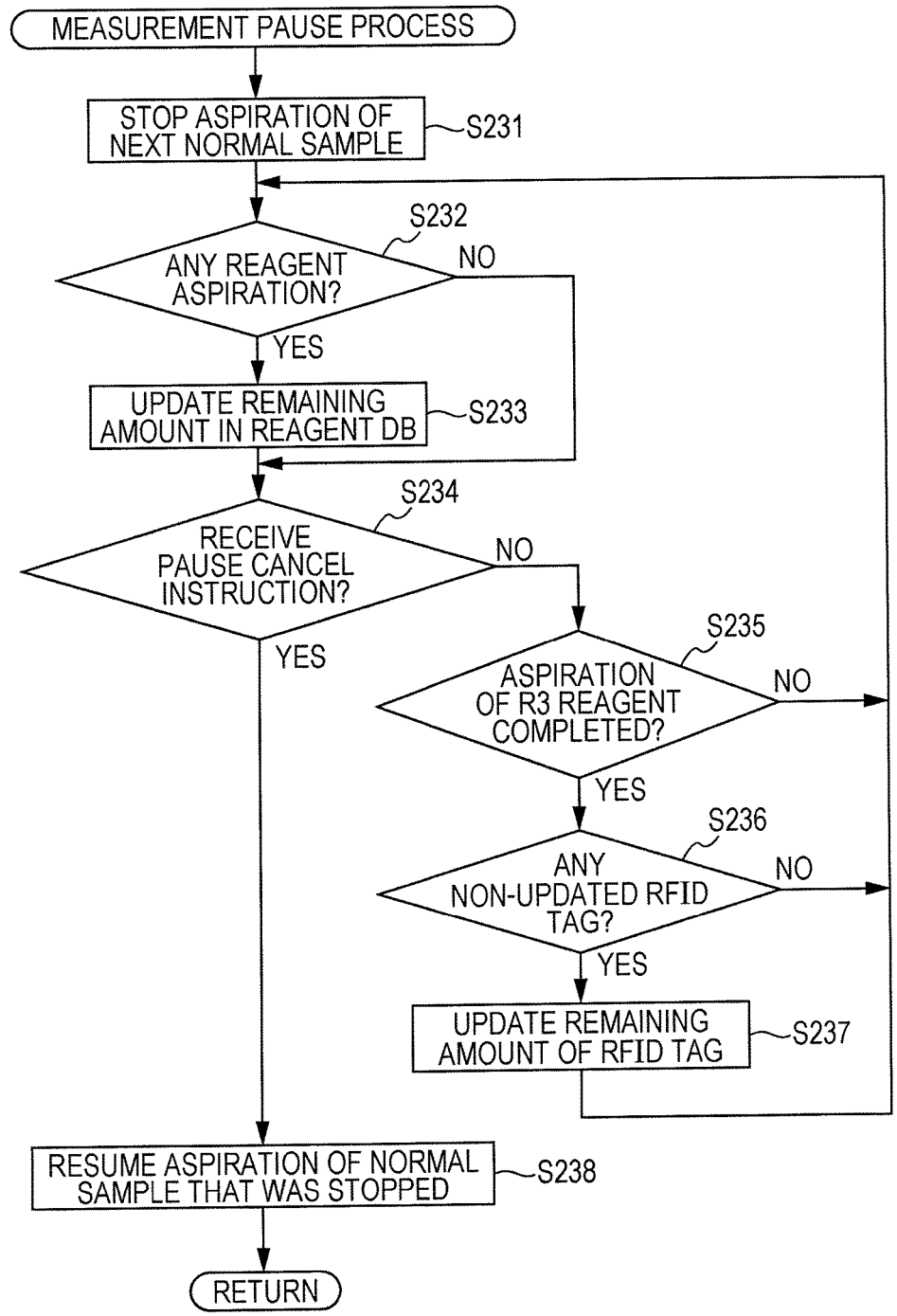
FIG. 14A is a flowchart showing a measurement pause process according to the embodiment.

FIG. 14A is a flowchart showing the "measurement pause process".

The CPU 201 first pauses the aspiration of the next normal sample at the sample aspirating position 1a (S231).

The CPU 201 then determines whether or not the reagent is aspirated from the R1 to R3 reagent containers (S232). If the reagents are aspirated from the R1 to R3 reagent containers (S232: YES), the CPU 201 updates (reduces) the remaining amount of R1 to R3 in the reagent DB stored in the RAM 203 according to the aspirating amount for the reagent container in which aspiration was carried out (S233).

The CPU 201 then determines whether or not the measurement pause cancel instruction is received from the control device 4 (S234). If the measurement pause cancel instruction is not received from the control device 4 (S234: NO), the CPU 201 determines whether or not the aspiration of the R3 reagent is completed for the sample currently being measured in the measurement mechanism section 2 (S235). If the aspiration of the R3 reagent is completed (S235: YES), the CPU 201 determines whether or not there is an RFID tag in which the remaining amount of reagent is not updated (S236). If there is an RFID tag in which the remaining amount of reagent is not updated (S236: YES), the CPU 201 writes the remaining amount in the reagent DB stored in the RAM 203 in the corresponding RFID tag 104, 114 through the antennas 162b, 163b (S237).

When receiving the measurement pause cancel instruction from the control device 4 (S224: YES), the CPU 201 resumes the aspiration of the normal sample that was stopped (S238).

Figure 14B:
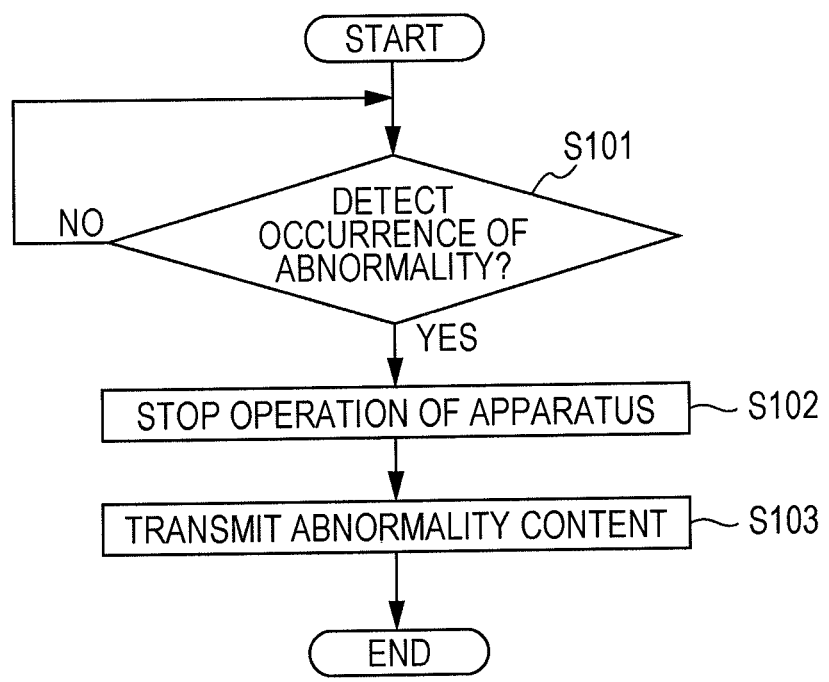
FIG. 14B is a flowchart showing an abnormality detection process by the measurement mechanism section according to the embodiment.

FIG. 14B is a flowchart showing the abnormality detection process by the measurement mechanism section 2. The abnormality detection process is executed in parallel to the measurement operation of FIG. 12.

When the occurrence of abnormality is detected in the measurement mechanism section 2 (S101: YES), the CPU 201 stops the operation of the measurement mechanism section 2 (S102), and transmits the abnormality content to the control device 4 (S103). The CPU 401 of the control device 4 displays an error help screen on the display unit 420 when receiving the abnormality content from the measurement mechanism section 2.

Figure 15:
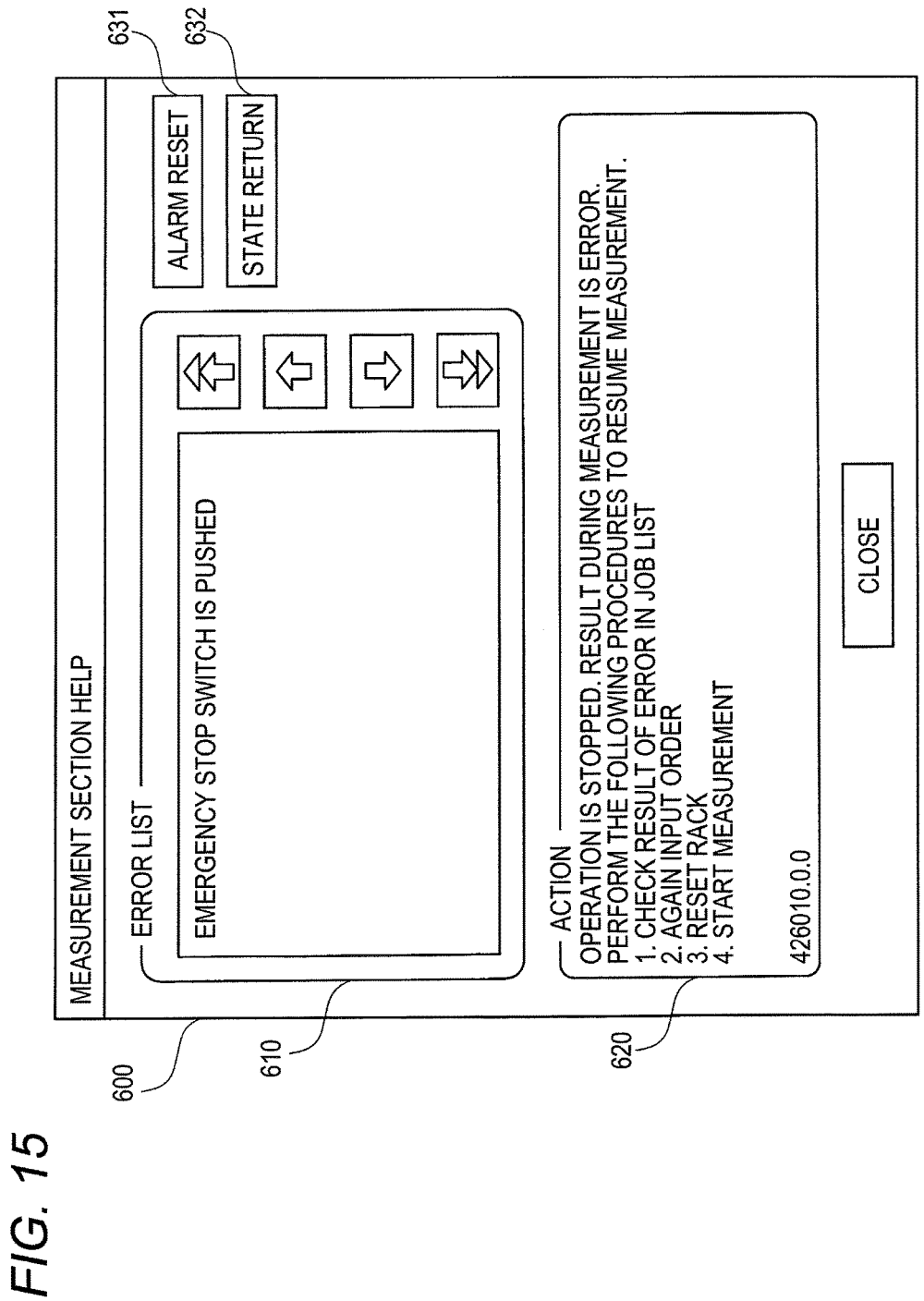
FIG. 15 is a view of an error help screen displayed on the display unit of the control device according to the embodiment.

FIG. 15 is a view of an error help screen displayed on the display unit 420 of the control device 4. An error help screen 600 includes an error display region 610, a description display region 620, an alarm reset button 631, and a state return button 632.

A list of errors that became the cause of occurrence of abnormality is displayed in the error display region 610. The description on the error selected in the error display region 610 and the countermeasure method for such error are displayed in the description display region 620. If the alarm reset button 631 is pushed when the alarm is issued due to the occurrence of abnormality, the alarm is stopped. When the state return button 632 is pushed, the occurred error is canceled.

Therefore, when the error display region 610 is displayed, the user recovers the error of the measurement mechanism section 2 by referencing the content of the description display region 620. When the state return button 632 is pushed by the user thereafter, the state return instruction is transmitted from the control device 4 to the measurement mechanism section 2. The CPU 201 of the measurement mechanism section 2 cancels the error of the measurement mechanism section 2 and resumes the continuous measurement shown in FIG. 12 as the state return from the abnormality.

The remaining amount in the reagent DB is simultaneously updated when the reagent is aspirated, and thus the remaining amount in the reagent DB of immediately before the occurrence of abnormality becomes the appropriate remaining amount. Therefore, the appropriate remaining amount is held in the RFID tag by writing the remaining amount in the reagent DB in the corresponding RFID tag in S17 of FIG. 12.

According to the present embodiment, the reading of the RFID tag is carried out at the time of the measurement preparation operation and at the time of installation of the new reagent container, and the writing of the RFID tag is carried out collectively at the time the dispensing of R1 to R3 reagents is completed in all measurements, at the time of changing the reagent container, at the time of pausing the measurement, and at the time of state return from the abnormality. The number of writing to the RFID tag thus can be reduced and the risk of occurrence of the write error can be reduced.

According to the present embodiment, the remaining amount of the reagent is stored in both the RFID tag of the reagent container and the storage unit of the analyzer. Therefore, even if the RFID tag is malfunctioning, the remaining amount of the reagent can be correctly managed since the remaining amount of the reagent is stored in the storage unit of the analyzer.

The embodiments of the present invention have been described above, but the embodiments of the present invention are not limited thereto.

The blood has been described as the measuring target in the above described embodiments, but urine may be the measuring target. In other words, the present invention can be applied to a specimen analyzer for testing urine, and the present invention can also be applied to a clinical sample examining apparatus for examining other clinical samples.

In the embodiments described above, the reagent DB is stored in the RAM 203 of the measurement mechanism section 2, but this is not the sole case, and the reagent DB may be stored in the hard disc separately arranged in the measurement mechanism section 2, or the RAM 403 and the hard disc 404 of the control device 4. The reagent DB may be stored in the RAM and the hard disc of other devices communicably connected to the specimen analyzer 1.

In the above described embodiment, the remaining amount of reagent is written to the RFID tag when all the aspiration of the R3 reagent in the continuous measurement is completed, but the present invention is not limited thereto. For instance, the remaining amount of reagent may be written to the RFID tag when all the dispensing of the R3 reagent to the cuvette in the continuous measurement is completed or when the continuous measurement is completed.

Various changes may be appropriately made on the embodiments of the present invention within the scope of the technical concept defined in the Claims.

What is claimed is:

1. A method performed by a sample analyzer configured to perform a plurality of measurements with respect to a plurality of samples, using a reagent container from which a reagent is aspirated into the plurality of samples, the method being performed using a processor and a detector, the method comprising:
   storing, by the processor, first information regarding a remaining amount of the reagent in the reagent container to a memory of the sample analyzer, the first information being read from a storage medium of the reagent container;
   controlling, by the processor, the sample analyzer to start performing a continuous measurement operation in which the plurality of measurements with respect to the plurality of samples is performed based on an aspiration of the reagent from the reagent container into the plurality of samples;
   updating, by the processor, the first information stored in the memory in response to the aspiration of the reagent from the reagent container while the continuous measurement operation with respect to the plurality of samples proceeds;
   determining, by the processor, that the aspiration of the reagent from the reagent container is completed for the continuous measurement operation with respect to the plurality of samples; and
   writing, by the processor, the updated first information from the memory to the storage medium based on the determining that the aspiration of the reagent from the reagent container for the continuous measurement operation with respect to the plurality of samples is completed,
   wherein the storage medium of the reagent container is writable and readable, and
   the writing the updated first information is postponed until the aspiration of the reagent from the reagent container for the continuous measurement operation with respect to the plurality of samples is completed.

2. The method according to claim 1, further comprising reading, by the processor, the first information in the storage medium before the continuous measurement operation with respect to the plurality of samples is started.

3. The method according to claim 1, wherein the storage medium of the reagent container is written and read at a first position of the sample analyzer,
   the reagent is aspirated from the reagent container at a second position of the sample analyzer, and
   the first position and the second position are differently located.

4. The method according to claim 1, further comprising:
   sequentially transporting sample containers accommodating the plurality of samples, respectively, to an aspirating position; and
   dispensing one of the plurality of samples accommodated in one of the sample containers which is transported to the aspirating position to a reaction container.

5. The method according to claim 1, further comprising:
   prior to the determining, receiving, by the processor, an instruction for a priority measurement while the continuous measurement operation with respect to the plurality of samples proceeds; and
   controlling, by the processor, the sample analyzer to perform the priority measurement,
   wherein the first information stored in the memory is updated in response to the aspiration of the reagent during the priority measurement, and the continuous measurement operation with respect to the plurality of samples is resumed based on a completion of the priority measurement.

6. The method according to claim 1, further comprising:
prior to the determining, receiving, by the processor, a reagent replacement instruction while the continuous measurement operation with respect to the plurality of samples proceeds,
wherein the first information stored in the memory is written to the storage medium based on the receiving the reagent replacement instruction, and
the continuous measurement operation with respect to the plurality of samples is resumed based on a completion of a reagent replacement.

7. The method according to claim 1, further comprising:
prior to the determining, receiving, by the processor, a pause instruction while the continuous measurement operation with respect to the plurality of samples proceeds; and
controlling, by the processor, the sample analyzer to pause the continuous measurement operation with respect to the plurality of samples,
wherein the first information stored in the memory is written to the storage medium based on the receiving the pause instruction, and
the continuous measurement operation with respect to the plurality of samples is resumed based on a pause cancel instruction being received.

8. The method according to claim 1, further comprising:
prior to the determining, detecting, by the processor, an abnormality of the sample analyzer while the continuous measurement operation with respect to the plurality of samples proceeds; and
stopping the continuous measurement operation with respect to the plurality of samples based on the detecting the abnormality,
wherein, based on detecting that the sample analyzer returned from the abnormality, the first information stored in the memory is written to the storage medium and the continuous measurement operation with respect to the plurality of samples is resumed.

9. The method according to claim 1, wherein the first information stored in the storage medium is read automatically.

10. The method according to claim 9, wherein the reagent container is one of a plurality of reagent containers held in a reagent container holder,
the first information is stored in the storage medium of each of the plurality of reagent containers, as corresponding pieces of the first information regarding the remaining amount of the reagent in the plurality of reagent containers, respectively, and
the corresponding pieces of the first information stored in the storage medium of each the plurality of reagent containers are read automatically.

11. The method according to claim 10, further comprising:
determining, by the processor, whether all of the storage medium of each of the plurality of reagent containers are updated based on the aspiration for the continuous measurement operation with respect to the plurality of samples being completed, and
based on the determining an un-updated storage medium of one of the plurality of reagent containers, writing, by the processor, the corresponding pieces of the first information regarding the remaining amount of the reagent in the one of the plurality of reagent containers, from the memory to the un-updated storage medium.

12. The method according to claim 1, further comprising decreasing the remaining amount of the first information stored in the memory according to an aspiration amount of the reagent.

13. The method according to claim 1, further comprising displaying the remaining amount of the reagent in the reagent container on a display of the sample analyzer.

14. The method according to claim 13, wherein the remaining amount of the reagent displayed on the display is updated based on the aspiration of the reagent.

15. The method according to claim 1, wherein the reagent container is one of a plurality of reagent containers which are arranged in a circle in the sample analyzer.

16. The method according to claim 1, wherein the performing the continuous measurement operation comprises:
detecting a reaction product which is produced when a component contained in one of the plurality of samples and the reagent are antigen-antibody reacted.

17. The method according to claim 1, wherein the storage medium includes a writable region and a read-only region, and
the first information indicating the remaining amount of the reagent in the reagent container is written into the writable region.

* * * * *